United States Patent
Manus et al.

(10) Patent No.: US 10,058,493 B2
(45) Date of Patent: Aug. 28, 2018

(54) ORAL CARE COMPOSITIONS AND METHODS OF USE

(71) Applicant: COLGATE-PALMOLIVE COMPANY, New York, NY (US)

(72) Inventors: Lisa Manus, Plainsboro, NJ (US); Julia Dreifus, Millstone, NJ (US)

(73) Assignee: Colgate-Palmolive Company, New York, NY (US)

(*) Notice: Subject to any disclaimer, the term of this patent is extended or adjusted under 35 U.S.C. 154(b) by 0 days.

(21) Appl. No.: 15/386,031

(22) Filed: Dec. 21, 2016

(65) Prior Publication Data
US 2018/0168960 A1  Jun. 21, 2018

(51) Int. Cl.
| | | |
|---|---|---|
| *A61Q 11/00* | (2006.01) | |
| *A61K 8/88* | (2006.01) | |
| *A61K 8/27* | (2006.01) | |
| *A61K 8/362* | (2006.01) | |
| *G01N 33/50* | (2006.01) | |
| *A61K 8/44* | (2006.01) | |
| *A61K 8/21* | (2006.01) | |
| *A61K 8/70* | (2006.01) | |
| *A61K 8/81* | (2006.01) | |

(52) U.S. Cl.
CPC ............ *A61K 8/27* (2013.01); *A61K 8/21* (2013.01); *A61K 8/362* (2013.01); *A61K 8/44* (2013.01); *A61K 8/70* (2013.01); *A61K 8/88* (2013.01); *A61Q 11/00* (2013.01); *G01N 33/50* (2013.01); *A61K 8/8152* (2013.01); *A61K 8/8164* (2013.01); *Y10S 514/901* (2013.01)

(58) Field of Classification Search
CPC . A61Q 11/00; A61K 8/21; A61K 8/70; A61K 8/8152; A61K 8/8164; A61K 8/88; A61K 8/27; A61K 8/44; A61K 8/362; Y10S 514/901; G01N 33/50
See application file for complete search history.

(56) References Cited

U.S. PATENT DOCUMENTS

| | | |
|---|---|---|
| 3,535,421 A | 10/1970 | Briner et al. |
| 3,678,154 A | 7/1972 | Widder et al. |
| 4,842,847 A | 6/1989 | Zahid et al. |
| 4,866,161 A | 9/1989 | Sikes et al. |
| 4,885,155 A | 12/1989 | Parran, Jr. et al. |
| 8,652,495 B2 | 2/2014 | Porter et al. |
| 9,486,396 B2 | 11/2016 | Maloney et al. |
| 9,532,932 B2 | 1/2017 | Prencipe et al. |
| 9,579,269 B2 | 2/2017 | Mello et al. |
| 9,682,026 B2 | 6/2017 | Kohli et al. |

(Continued)

FOREIGN PATENT DOCUMENTS

| | | |
|---|---|---|
| WO | WO 2011/123123 | 10/2011 |
| WO | WO 2011/162756 | 12/2011 |

(Continued)

OTHER PUBLICATIONS

Foam Stability in a Glycerol System. Journal of Colloid and Interface Science, 1989, vol. 127, Issue 2, pp. 573-582.

(Continued)

*Primary Examiner* — Jennifer Wecker

(57) ABSTRACT

This invention relates to oral care compositions comprising arginine, zinc citrate and zinc oxide, and an orally acceptable carrier, as well as to methods of using and of making these compositions.

18 Claims, 23 Drawing Sheets

(56) References Cited

U.S. PATENT DOCUMENTS

| | | |
|---|---|---|
| 9,682,027 B2 | 6/2017 | Prencipe et al. |
| 2004/0146466 A1* | 7/2004 | Baig .................. A23G 4/06 424/49 |
| 2009/0202454 A1 | 8/2009 | Prencipe et al. |
| 2013/0078197 A1* | 3/2013 | Mello .................. A61K 8/19 424/54 |
| 2013/0224126 A1* | 8/2013 | Lewus .................. A61K 8/347 424/52 |
| 2013/0330283 A1 | 12/2013 | Vogt et al. |
| 2015/0297500 A1 | 10/2015 | Robinson et al. |
| 2015/0313813 A1* | 11/2015 | Rege .................. A61K 8/27 424/52 |
| 2016/0000664 A1* | 1/2016 | Dehghan .................. A61K 8/24 424/52 |
| 2016/0317409 A1 | 11/2016 | Precipe et al. |
| 2016/0338921 A1* | 11/2016 | Prencipe .................. A61K 8/27 |
| 2017/0100312 A1 | 4/2017 | Precipe et al. |
| 2017/0224595 A1 | 8/2017 | Xu et al. |
| 2017/0367939 A1 | 12/2017 | Thomson et al. |
| 2017/0367946 A1 | 12/2017 | Rege et al. |
| 2017/0367947 A1 | 12/2017 | Rege et al. |
| 2017/0367948 A1 | 12/2017 | Thomson et al. |
| 2017/0367949 A1 | 12/2017 | Rege et al. |
| 2017/0367953 A1 | 12/2017 | Chen et al. |
| 2017/0368376 A1 | 12/2017 | Yang et al. |

FOREIGN PATENT DOCUMENTS

| | | | |
|---|---|---|---|
| WO | WO 2014/088575 | 6/2014 | |
| WO | WO 2014/098813 | 6/2014 | |
| WO | WO 2014/098814 | 6/2014 | |
| WO | WO 2014/098822 | 6/2014 | |
| WO | WO 2014/098824 | 6/2014 | |
| WO | WO 2014/098825 | 6/2014 | |
| WO | WO 2014088575 A1 * | 6/2014 | ............... A61K 8/27 |
| WO | WO 2015/094849 | 6/2015 | |
| WO | WO 2016/058140 | 4/2016 | |
| WO | WO 2016/105440 | 6/2016 | |
| WO | WO 2017/000837 | 1/2017 | |
| WO | WO 2017/003844 | 1/2017 | |
| WO | WO 2017/003856 | 1/2017 | |
| WO | 2017219339 | 12/2017 | |
| WO | 2017222548 | 12/2017 | |

OTHER PUBLICATIONS

Unpublished PCT application serial No. PCT/CN2016/086995, filed Jun. 24, 2016, 30 pages.

* cited by examiner

ORAL CARE COMPOSITIONS AND METHODS OF USE

FIELD

This invention relates to oral care compositions comprising arginine or salt thereof, zinc oxide and zinc citrate, and an orally acceptable carrier, as well as to methods of using and of making these compositions.

BACKGROUND

Natural buffering capacity of human saliva is controlled principally by the carbonic acid/bicarbonate system. Upon acid exposure from an external source (soft drinks, fruit juices, coffee) or internal source (stomach acid), this chemical system aids in neutralizing saliva toward higher pH values, which protects enamel. Poor saliva buffering capacity can cause poor oral health including increased risk for enamel erosion, caries, and high levels of oral bacteria. Arginine and other basic amino acids have been proposed for use in oral care and are believed to have significant benefits in combating cavity formation and tooth sensitivity. Commercially available arginine-based toothpaste contains arginine bicarbonate and precipitated calcium carbonate, but not fluoride. The carbonate ion is believed to have cariostatic properties, and the calcium is believed to form in complex with arginine to provide a protective effect.

However, the formulation of certain oral care compositions presents special challenges. For example, not all preservatives are active at higher pH. Some preservatives negatively affect the taste or aesthetics of the product. While certain preservatives, such as ethanol or parabens, are known to be effective at a range of pHs, these preservatives are not suitable for all products or all markets.

Zinc formulations also present challenges. Zinc is a well-known antimicrobial agent used in toothpaste compositions. Zinc is also a well-known essential mineral for human health, and has been reported to help strengthen dental enamel and to promote cell repair. Unfortunately, conventional toothpaste formulations often require a high concentrations of zinc, e.g., 2% by weight or more, to achieve efficacy. At this concentration, the zinc imparts a notably astringent taste to the composition.

Accordingly, there is a need for improved oral care compositions that promote rapid and/or sustained buffering capacity of saliva.

BRIEF SUMMARY

It has been found that the combination of a basic amino acid (i.e., arginine) and one or more sources of zinc (i.e., zinc oxide and zinc citrate, e.g., zinc citrate trihydrate) provides surprisingly effective buffering effects to counteract acidic conditions in the oral cavity.

Therefore, in one aspect, disclosed is an oral care composition (Composition 1.0) comprising:
 a. Basic amino acid in free or salt form, wherein the basic amino acid is arginine (e.g., free form arginine);
 b. zinc oxide and zinc citrate; and
 c. an orally acceptable carrier.

For example, the invention contemplates any of the following compositions (unless otherwise indicated, values are given as percentage of the overall weight of the composition)

1.1 Composition 1, wherein the composition maintains a pH over 5.0 (e.g., about 5.2) when challenged in an acidic aqueous solution with a cola beverage in an amount of about 90% v/v (e.g., about 91%) based on the total volume of the solution.

1.2 Composition 1 or 1.1, wherein the composition maintains a pH over 3.9 (e.g., about 3.92 or 4.0) when challenged in an acidic aqueous solution with a cola beverage in an amount of about 90% v/v (e.g., about 91%) based on the total volume of the solution.

1.3 Any of the preceding compositions, wherein the composition maintains a pH over 3.0 (e.g., about 3.3) when challenged in an acidic aqueous solution with a cola beverage in an amount of about 90% v/v (e.g., about 91%) based on the total volume of the solution.

1.4 Any of the preceding compositions, wherein the composition maintains a pH over 5.5 (e.g., about 5.5, 5.6 or 5.7) when challenged in an acidic aqueous solution with a cola beverage in an amount of about 80% v/v (e.g., about 83%) based on the total volume of the solution.

1.5 Any of the preceding compositions, wherein the composition maintains a pH over 4.0 (e.g., about 4.2, 4.3, 4.4 or 4.5) when challenged in an acidic aqueous solution with orange juice in an amount of about 55% v/v (e.g., about 55.5%) based on the total volume of the solution.

1.6 Any of the preceding compositions, wherein the composition maintains a pH over 6.0 (e.g., about 6.1) when challenged in an acidic aqueous solution with orange juice in an amount of about 33% v/v (e.g., about 33.3%) based on the total volume of the solution.

1.7 Any of the preceding compositions, wherein the composition maintains a pH over 5.0 (e.g., about 5.1 or 5.6) when challenged in an acidic aqueous solution with orange juice in an amount of about 33% v/v (e.g., about 33.3%) based on the total volume of the solution.

1.8 Any of the preceding compositions, wherein the composition maintains a pH over 7.0 (e.g., about 7.1, 7.2, 7.3, 7.4, 7.5, 7.6, 7.7, 7.8 or 7.9) when challenged in an acidic aqueous solution with 0.01M HCl in an amount of about 60% v/v based on the total volume of the solution.

1.9 Any of the preceding compositions, wherein the composition maintains a pH over 8.0 (e.g., about 8.1, 8.2, 8.3, 8.4, 8.5, 8.6, 8.7, 8.8 or 8.9) when challenged in an acidic aqueous solution with 0.01M HCl in an amount of about 60% v/v based on the total volume of the solution.

1.10 Any of the preceding compositions, wherein the composition maintains a pH over 7.0 (e.g., about 7.1, 7.2, 7.3, 7.4, 7.5, 7.6, 7.7, 7.8 or 7.9) 6 hours after sucrose challenge.

1.11 Any of the preceding compositions, wherein the composition maintains a pH over 8.0 (e.g., about 8.1, 8.2, 8.3, 8.4, 8.5, 8.6, 8.7, 8.8 or 8.9) 6 hours after sucrose challenge.

1.12 Any of the preceding compositions, wherein the composition maintains a pH over 9.0 (e.g., about 9.1, 9.2, 9.3, 9.4, 9.5, 9.6, 9.7, 9.8 or 9.9) 6 hours after sucrose challenge.

1.13 Any of the preceding compositions, wherein the composition maintains a pH over 7.0 (e.g., about 7.1, 7.2, 7.3, 7.4, 7.5, 7.6, 7.7, 7.8 or 7.9) 24 hours after sucrose challenge.

1.14 Any of the preceding compositions, wherein the composition maintains a pH over 8.0 (e.g., about 8.1, 8.2, 8.3, 8.4, 8.5, 8.6, 8.7, 8.8 or 8.9) 24 hours after sucrose challenge.

1.15 Any of the preceding compositions, wherein the composition maintains a pH over 9.0 (e.g., about 9.1, 9.2, 9.3, 9.4, 9.5, 9.6, 9.7, 9.8 or 9.9) 24 hours after sucrose challenge.

1.16 Composition 1.0 wherein the basic amino acid has the L-configuration (e.g., L-arginine).

1.17 Any of the preceding compositions wherein the arginine is in free form.

1.18 Any of the preceding compositions wherein the basic amino acid is provided in the form of a di- or tri-peptide comprising arginine, or salts thereof 1.19 Any of the preceding compositions wherein the arginine is present in an amount corresponding to 1% to 15%, e.g., 3 wt. % to 10 wt. % of the total composition weight, about e.g., 1.5%, 4%, 5%, or 8%, wherein the weight of the basic amino acid is calculated as free form.

1.20 Any of the preceding compositions wherein the arginine is present in an amount from 0.1 wt. %-6.0 wt. %. (e.g., about 1.5 wt %).

1.21 Any of the preceding compositions wherein the arginine is present in an amount of about 1.5 wt. %.

1.22 Any of the preceding compositions wherein the amino acid is L-arginine.

1.23 Any of the preceding compositions wherein the amino acid is free form arginine.

1.24 Any of the preceding compositions wherein the amino acid is arginine phosphate.

1.25 Any of the preceding compositions wherein the amino acid is arginine hydrochloride.

1.26 Any of the preceding compositions wherein the amino acid is arginine bicarbonate.

1.27 Any of the preceding compositions wherein the amino acid is arginine ionized by neutralization with an acid or a salt of an acid.

1.28 Any of preceding compositions wherein the composition is ethanol-free.

1.29 Any of the preceding compositions further comprising a fluoride source selected from: stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.

1.30 Any of the preceding compositions wherein the fluoride source is sodium fluoride.

1.31 Any of the preceding compositions wherein the fluoride source is a fluoride salt present in an amount of 0.1 wt. % to 2 wt. % (0.1 wt %-0.6 wt. %) of the total composition weight (e.g., sodium fluoride (e.g., about 0.32 wt. %).

1.32 Any of the preceding compositions wherein the fluoride source is a soluble fluoride salt which provides fluoride ion in an amount of from 50 to 25,000 ppm (e.g., 750-2000 ppm, e.g., 1000-1500 ppm, e.g., about 1000 ppm, e.g., about 1450 ppm)

1.33 Any of the preceding compositions wherein the fluoride source is sodium fluoride which provides fluoride in an amount from 750-2000 ppm (e.g., about 1450 ppm)

1.34 Any of the preceding compositions wherein the fluoride source is sodium fluoride and which provides fluoride in an amount from 1000 ppm-1500 ppm.

1.35 Any of the preceding compositions wherein the fluoride source is sodium fluoride and which provides fluoride in an amount of about 1450 ppm.

1.36 Any of the preceding compositions wherein the pH is between 7.5 and 10.5, e.g., 8-9.5, e.g., 7.2-9.0, about 8.0, about 9.0.

1.37 Any of the preceding compositions further comprising calcium carbonate and/or precipitated calcium carbonate.

1.38 Any of the preceding compositions further comprising an effective amount of one or more alkali phosphate salts, e.g., sodium, potassium or calcium salts, e.g., selected from alkali dibasic phosphate and alkali pyrophosphate salts, e.g., alkali phosphate salts selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, disodium hydrogenorthophoshpate, monosodium phosphate, pentapotassium triphosphate and mixtures of any of two or more of these, e.g., in an amount of 0.1-20%, e.g., 0.1-8%, e.g., e.g., 0.2 to 5%, e.g., 0.3 to 2%, e.g., 0.3 to 1%, e.g about 0.5%, about 1%, about 2%, about 5%, about 6%, by weight of the composition.

1.39 Any of the preceding compositions comprising tetrapotassium pyrophoshpate, disodium hydrogenorthophoshpate, monosodium phosphate, and pentapotassium triphosphate.

1.40 Any of the preceding compositions comprising a polyphosphate.

1.41 The composition of 1.40, wherein the polyphosphate is tetrasodium pyrophosphate.

1.42 The composition of 1.42, wherein the tetrasodium pyrophosphate is from 0.1-1.0 wt % (e.g., about 0.5 wt %).

1.43 Any of the preceding compositions further comprising an abrasive or particulate (e.g., silica).

1.44 Any of the preceding compositions wherein the silica is synthetic amorphous silica (e.g., 1%-28% by wt.) (e.g., 8%-25% by wt.).

1.45 Any of the preceding composition wherein the silica abrasives are silica gels or precipitated amorphous silicas, e.g. silicas having an average particle size ranging from 2.5 microns to 12 microns.

1.46 Any of the preceding compositions further comprising a small particle silica having a median particle size (d50) of 1-5 microns (e.g., 3-4 microns) (e.g., about 5 wt. % Sorbosil AC43 from PQ Corporation, Warrington, United Kingdom).

1.47 Any of the preceding compositions wherein 20-30 wt % of the total silica in the composition is small particle silica (e.g., having a median particle size (d50) of 3-4 microns) and wherein the small particle silica is about 5 wt. % of the oral care composition.

1.48 Any of the preceding compositions comprising silica wherein the silica is used as a thickening agent, e.g., particle silica.

1.49 Any of the preceding compositions further comprising a nonionic surfactant, wherein the nonionic surfactant is in an amount of from 0.5-5%, e.g, 1-2%, selected from poloxamers (e.g., poloxamer 407), polysorbates (e.g., polysorbate 20), polyoxyl hydrogenated castor oil (e.g., polyoxyl 40 hydrogenated castor oil), and mixtures thereof 1.50 Composition 1.50, wherein the poloxamer nonionic surfactant has a polyoxypropylene molecular mass of from 3000 to 5000 g/mol and a polyoxyethylene content of from 60 to 80 mol %, e.g., the poloxamer nonionic surfactant comprises poloxamer 407.

1.51 Any of the preceding compositions, wherein the ratio of the amount of zinc oxide (e.g., wt. %) to zinc citrate (e.g., wt %) is from 1.5:1 to 4.5:1 (e.g., 2:1, 2.5:1, 3:1, 3.5:1, or 4:1).

1.52 Any of the preceding compositions, wherein the zinc citrate is in an amount of from 0.25 to 1.0 wt % (e.g., 0.5 wt. %) and zinc oxide may be present in an amount of from 0.75 to 1.25 wt % (e.g., 1.0 wt. %) based on the weight of the oral care composition.

1.53 Any of the preceding compositions wherein the zinc citrate is about 0.5 wt %.

1.54 Any of the preceding compositions wherein the zinc oxide is about 1.0 wt %.

1.55 Any of the preceding compositions where the zinc citrate is about 0.5 wt % and the zinc oxide is about 1.0 wt %.

1.56 Any of the preceding compositions wherein the benzyl alcohol is present from 0.1-0.6 wt %., (e.g., 0.1-0.4 wt %) e.g. about 0.1 wt. %, about 0.2 wt. %, or about 0.3 wt. %.

1.57 Any of the preceding compositions wherein the benzyl alcohol is about 0.1 wt %.

1.58 Any of the preceding composition wherein benzyl alcohol is present at is considered a preservative.

1.59 Any of the preceding compositions comprising polymer films.

1.60 Any of the preceding compositions comprising flavoring, fragrance and/or coloring agent.

1.61 The composition of 1.61, wherein the flavoring agent is sodium saccharin, sucralose, or a mixture thereof 1.62 Any of the preceding compositions, wherein the composition comprises a thickening agent selected from the group consisting of carboxyvinyl polymers, carrageenan, xanthan, hydroxyethyl cellulose and water soluble salts of cellulose ethers (e.g., sodium carboxymethyl cellulose and sodium carboxymethyl hydroxyethyl cellulose).

1.63 Any of the preceding compositions, wherein the composition comprises sodium carboxymethyl cellulose (e.g., from 0.5 wt. %-1.5 wt. %).

1.64 Any of the preceding compositions comprising from 5%-40%, e.g., 10%-35%, e.g., about 15%, 25%, 30%, and 35% water.

1.65 Any of the preceding compositions comprising an additional antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, Zinc Chloride, Zinc Lactate, Zinc Sulfate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing.

1.66 Any of the preceding compositions comprising an antioxidant, e.g., selected from the group consisting of Co-enzyme Q10, PQQ, Vitamin C, Vitamin E, Vitamin A, BHT, anethole-dithiothione, and mixtures thereof.

1.67 Any of the preceding compositions comprising a whitening agent.

1.68 Any of the preceding compositions comprising a whitening agent selected from a whitening active selected from the group consisting of peroxides, metal chlorites, perborates, percarbonates, peroxyacids, hypochlorites, and combinations thereof 1.69 Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate), or hydrogen peroxide polymer complexes such as hydrogen peroxide-polyvinyl pyrrolidone polymer complexes.

1.70 Any of the preceding compositions, wherein the glycerin is in an amount from 20%-40% by wt. of the composition.

1.71 Any of the preceding compositions, wherein the composition further comprises sorbitol.

1.72 The composition of 1.72, wherein the sorbitol is from 10%-20% by wt. of the composition.

1.73 Any of the preceding compositions further comprising an agent that interferes with or prevents bacterial attachment, e.g., ethyl lauroyl arginiate (ELA) or chitosan.

1.74 Any of the preceding compositions comprising:
  a. about 1.0% zinc oxide
  b. about 0.5% zinc citrate
  c. about 1.5% L-arginine
  d. about 0.32% sodium fluoride;
  e. about 35% glycerin;

1.75 Any of compositions 1.0-1.81 comprising:
  a. about 1.0% zinc oxide
  b. about 0.5% zinc citrate
  c. about 5% L-arginine
  d. about 0.32% sodium fluoride;
  e. about 26% glycerin; and
  f. about 13% sorbitol;

1.76 Any of the preceding compositions effective upon application to the oral cavity, e.g., by rinsing, optionally in conjunction with brushing, to (i) reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of arginolytic bacteria, (ix) inhibit microbial biofilm formation in the oral cavity, (x) raise and/or maintain plaque pH at levels of at least pH 5.5 following sugar challenge, (xi) reduce plaque accumulation, (xii) treat, relieve or reduce dry mouth, (xiii) clean the teeth and oral cavity (xiv) reduce erosion, (xv) prevents stains and/or whiten teeth, (xvi) immunize the teeth against cariogenic bacteria; and/or (xvii) promote systemic health, including cardiovascular health, e.g., by reducing potential for systemic infection via the oral tissues.

1.77 Any of the preceding oral compositions, wherein the oral composition may be any of the following oral compositions selected from the group consisting of: a toothpaste or a dentifrice, a mouthwash or a mouth rinse, a topical oral gel, and a denture cleanser.

1.78 A composition obtained or obtainable by combining the ingredients as set forth in any of the preceding compositions.

A composition obtained or obtainable by combining the ingredients as set forth in any of the preceding compositions.

A composition for use as set for in any of the preceding compositions.

In another embodiment, the invention encompasses a method (Method 1) to improve oral health comprising applying an effective amount of the oral composition of any of the embodiments set forth above to the oral cavity of a subject in need thereof, e.g., a method to
 i. reduce or inhibit formation of dental caries,
 ii. reduce, repair or inhibit early enamel lesions, e.g., as detected by quantitative light-induced fluorescence (QLF) or electrical caries measurement (ECM),
 iii. reduce or inhibit demineralization and promote remineralization of the teeth,
 iv. reduce hypersensitivity of the teeth,
 v. reduce or inhibit gingivitis,
 vi. promote healing of sores or cuts in the mouth,
 vii. reduce levels of acid producing bacteria,
 viii. to increase relative levels of arginolytic bacteria,
 ix. inhibit microbial bio film formation in the oral cavity,
 x. raise and/or maintain plaque pH at levels of at least pH 5.5 following sugar challenge,
 xi. reduce plaque accumulation,
 xii. treat dry mouth,
 xiii. enhance systemic health, including cardiovascular health, e.g., by reducing potential for systemic infection via the oral tissues,
 xiv. Whiten teeth,
 xv. reduce erosion of the teeth,
 xvi. immunize (or protect) the teeth against cariogenic bacteria and their effects, and/or
 xvii. clean the teeth and oral cavity.

In another embodiment, the invention relates to a method to identify candidate oral care buffering agents, compositions, solutions or systems useful to mitigate acidic conditions in the oral cavity. (Method 2)

Therefore, method 2 includes 2.1. A ex vivo method to identify candidate oral care buffering agents, compositions, solutions or systems useful to mitigate acidic conditions in the oral cavity comprising the steps of providing a first sample and a second sample, e.g., saliva, wherein the first and second samples have the same initial pH; contacting the first sample with a measured quantity of acidic substance, e.g., cola, coffee, wine, orange juice or aqueous acids (i.e., 1% HCl solution) to form a solution; contacting the first sample with a candidate oral care buffering agent, composition, solution or system; determining whether the pH of the first sample solution has changed; contacting the second sample with the measured quantity of acidic substance to form a solution; contacting the second sample with any of Composition 1, et seq.; determining whether the pH of the second sample solution has changed, wherein an increase in pH greater in the first sample being greater than or equal to that of the second sample indicates that the candidate oral care buffering agents, compositions, solutions or systems can be useful to mitigate acidic conditions in the oral cavity.

2.2 An ex vivo method to identify candidate oral care buffering agents, compositions, solutions or systems useful to mitigate acidic conditions in the oral cavity comprising the steps of providing a first sample and a second sample, e.g., enamel from a human or bovine source; contacting the first sample with a measured quantity of acidic substance, e.g., cola, coffee, wine, orange juice or aqueous acids (i.e., 1% HCl solution); contacting the first sample with a candidate oral care buffering agent, composition, solution or system; determining whether acid erosion has occurred to the first sample; contacting the second sample with the measured quantity of acidic substance; contacting the second sample with any of Composition 1, et seq.; determining whether acid erosion has occurred to the second sample, wherein acid erosion of the first sample being less than or equal to that of the second sample indicates that the candidate oral care buffering agents, compositions, solutions or systems can be useful to mitigate acidic conditions in the oral cavity.

2.3 An ex vivo method to identify candidate oral care buffering agents, compositions, solutions or systems useful to mitigate acidic conditions in the oral cavity comprising the steps of providing a first sample and a second sample, e.g., saliva, wherein the first and second samples have the same initial pH; contacting the first sample with a measured quantity of a sugar, e.g., sucrose to form a solution; contacting the first sample with a candidate oral care buffering agent, composition, solution or system; determining whether the pH of the first sample solution has changed; contacting the second sample with the measured quantity of sugar to form a solution; contacting the second sample with any of Composition 1, et seq.; determining whether the pH of the second sample solution has changed, wherein an increase in pH greater in the first sample that being greater than or equal to that of the second sample indicates that the candidate oral care buffering agents, compositions, solutions or systems can be useful to mitigate acidic conditions in the oral cavity.

The invention further relates to a method to treat acid-related conditions in the oral cavity, comprising administering to a subject any of Composition 1, et seq.

BRIEF DESCRIPTION OF THE FIGURES

In part, other aspects, features, benefits and advantages of the embodiments described herein will be apparent with regard to the following description, appended claims and accompanying figures.

DETAILED DESCRIPTION

Figure 1:
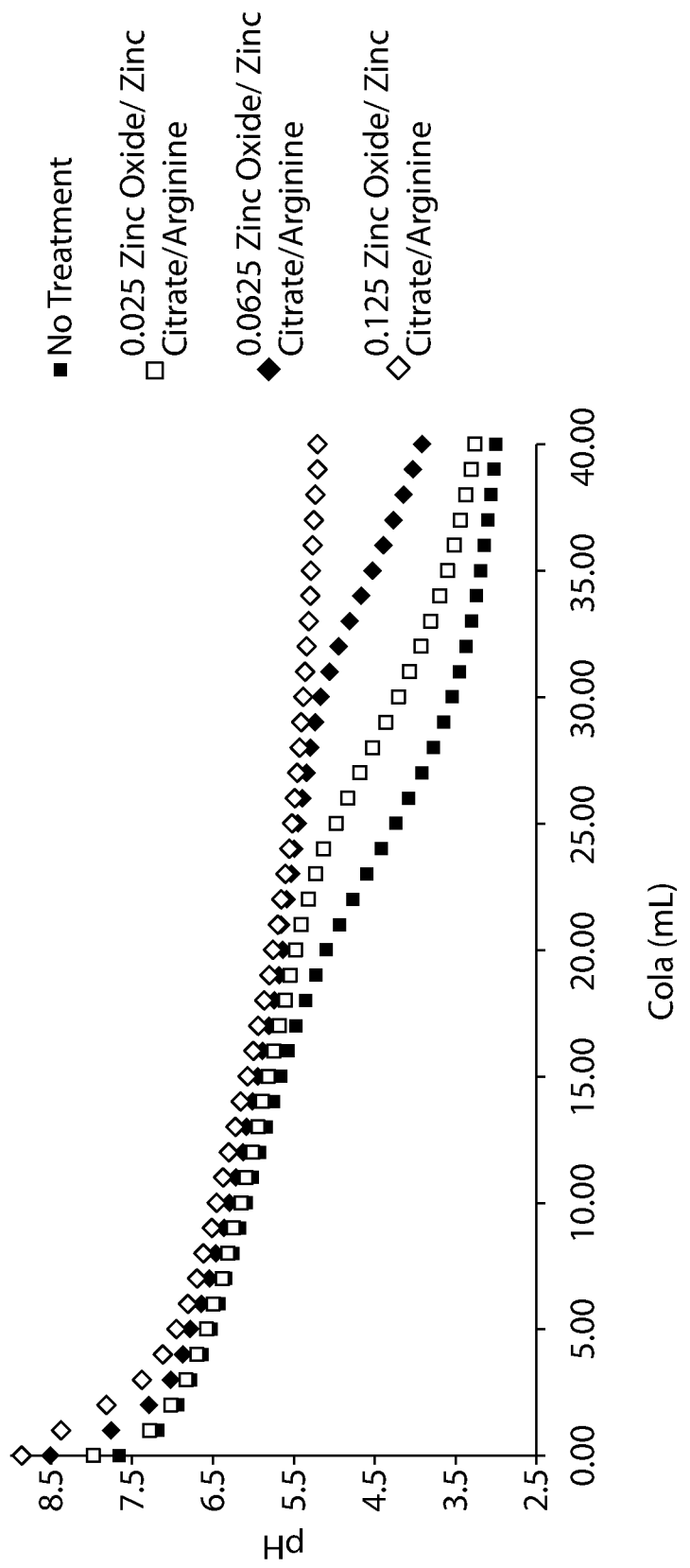
FIG. 1 illustrates the pH of whole saliva treated with zinc oxide/zinc citrate/arginine solutions before and after acid challenge with a cola beverage as a function of volume of cola added to the solution, where the solutions having varying concentrations of zinc oxide/zinc citrate/arginine.

As used herein, the term "oral composition" means the total composition that is delivered to the oral surfaces. The composition is further defined as a product which, during the normal course of usage, is not, the purposes of systemic administration of particular therapeutic agents, intentionally swallowed but is rather retained in the oral cavity for a time sufficient to contact substantially all of the dental surfaces and/or oral tissues for the purposes of oral activity. Examples of such compositions include, but are not limited to, toothpaste or a dentifrice, a mouthwash or a mouth rinse, a topical oral gel, a denture cleanser, and the like.

As used herein, the term "dentifrice" means paste, gel, or liquid formulations unless otherwise specified. The dentifrice composition can be in any desired form such as deep striped, surface striped, multi-layered, having the gel surrounding the paste, or any combination thereof. Alternatively the oral composition may be dual phase dispensed from a separated compartment dispenser.

Basic Amino Acids

The basic amino acids which can be used in the compositions and methods of the invention include not only naturally occurring basic amino acids, such as arginine, lysine, and histidine, but also any basic amino acids having a carboxyl group and an amino group in the molecule, which are water-soluble and provide an aqueous solution with a pH of 7 or greater.

Accordingly, basic amino acids include, but are not limited to, arginine, lysine, serine, citrullene, ornithine, creatine, histidine, diaminobutanoic acid, diaminoproprionic acid, salts thereof or combinations thereof. In a particular embodiment, the basic amino acids are selected from arginine, citrullene, and ornithine.

In certain embodiments, the basic amino acid is arginine, for example, L-arginine, or a salt thereof.

The compositions of the invention (e.g., Composition 1.0 et seq) are intended for topical use in the mouth and so salts for use in the present invention should be safe for such use, in the amounts and concentrations provided. Suitable salts include salts known in the art to be pharmaceutically acceptable salts are generally considered to be physiologically acceptable in the amounts and concentrations provided. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion.

Fluoride Ion Source

The oral care compositions (e.g., Composition 1.0 et seq) may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., each of which are incorporated herein by reference. Representative fluoride ion sources used with the present invention (e.g., Composition 1.0 et seq.) include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. Where the formulation comprises calcium salts, the fluoride salts are preferably salts wherein the fluoride is covalently bound to another atom, e.g., as in sodium monofluorophosphate, rather than merely ionically bound, e.g., as in sodium fluoride.

Surfactants

The invention may in some embodiments contain anionic surfactants, e.g., the Compositions of Composition 1.0, et seq., for example, water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomo-glyceride sulfate; higher alkyl sulfates, such as sodium lauryl sulfate; higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or, for example sodium laureth-2 sulfate $(CH_3(CH2)_{10}CH_2(OCH_2CH_2)_2OSO_3Na)$; higher alkyl aryl sulfonates such as sodium dodecyl benzene sulfonate (sodium lauryl benzene sulfonate); higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate. By "higher alkyl" is meant, e.g., $C_{6-30}$ alkyl. In particular embodiments, the anionic surfactant (where present) is selected from sodium lauryl sulfate and sodium ether lauryl sulfate. When present, the anionic surfactant is present in an amount which is effective, e.g., >0.001% by weight of the formulation, but not at a concentration which would be irritating to the oral tissue, e.g., 1%, and optimal concentrations depend on the particular formulation and the particular surfactant. In one embodiment, the anionic surfactant is present at from 0.03% to 5% by weight, e.g., 1.5%.

In another embodiment, cationic surfactants useful in the present invention can be broadly defined as derivatives of aliphatic quaternary ammonium compounds having one long alkyl chain containing 8 to 18 carbon atoms such as lauryl trimethylammonium chloride, cetyl pyridinium chloride, cetyl trimethylammonium bromide, di-isobutylphenoxyethyldimethylbenzylammonium chloride, coconut alkyltrimethylammonium nitrite, cetyl pyridinium fluoride, and mixtures thereof. Illustrative cationic surfactants are the quaternary ammonium fluorides described in U.S. Pat. No. 3,535,421, to Briner et al., herein incorporated by reference. Certain cationic surfactants can also act as germicides in the compositions.

Illustrative nonionic surfactants of Composition 1.0, et seq., that can be used in the compositions of the invention can be broadly defined as compounds produced by the condensation of alkylene oxide groups (hydrophilic in nature) with an organic hydrophobic compound which may be aliphatic or alkylaromatic in nature. Examples of suitable nonionic surfactants include, but are not limited to, the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials. In a particular embodiment, the composition of the invention comprises a nonionic surfactant selected from poloxamers (e.g., poloxamer 407), polysorbates (e.g., polysorbate 20), polyoxyl hydrogenated castor oils (e.g., polyoxyl 40 hydrogenated castor oil), and mixtures thereof.

Illustrative amphoteric surfactants of Composition 1.0, et seq., that can be used in the compositions of the invention include betaines (such as cocamidopropylbetaine), derivatives of aliphatic secondary and tertiary amines in which the aliphatic radical can be a straight or branched chain and wherein one of the aliphatic substituents contains about 8-18 carbon atoms and one contains an anionic water-solubilizing group (such as carboxylate, sulfonate, sulfate, phosphate or phosphonate), and mixtures of such materials.

The surfactant or mixtures of compatible surfactants can be present in the compositions of the present invention (e.g., Composition 1.0 et seq) in 0.1% to 5%, in another embodiment 0.3% to 3% and in another embodiment 0.5% to 2% by weight of the total composition.

Flavoring Agents

The oral care compositions of the invention may also include a flavoring agent. Flavoring agents which are used in the practice of the present invention include, but are not limited to, essential oils and various flavoring aldehydes, esters, alcohols, and similar materials, as well as sweeteners such as sodium saccharin. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint.

The flavoring agent is incorporated in the oral composition (e.g., Composition 1.0 et seq) at a concentration of 0.01 to 2% by weight.

Chelating and Anti-Calculus Agents

The oral care compositions of the invention also may include one or more chelating agents able to complex calcium found in the cell walls of the bacteria. Binding of this calcium weakens the bacterial cell wall and augments bacterial lysis.

Another group of agents suitable for use as chelating or anti-calculus agents in the present invention are the soluble pyrophosphates. The pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide least 0.1 wt. % pyrophosphate ions, e.g., 0.1 to 3 wt 5, e.g., 0.1 to 2 wt %, e.g., 0.1 to 1 wt %, e.g., 0.2 to 0.5 wt %. The pyrophosphates also contribute to preservation of the compositions by lowering water activity.

Polymers

The oral care compositions of the invention also optionally include one or more polymers, such as polyethylene glycols, polyvinyl methyl ether maleic acid copolymers, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts. Certain embodiments include 1:4 to 4:1 copolymers of maleic anhydride or acid with another polymerizable ethylenically unsaturated monomer, for example, methyl vinyl ether (methoxyethylene) having a molecular weight (M.W.) of about 30,000 to about 1,000,000. These copolymers are available for example as Gantrez AN 139 (M.W. 500,000), AN 1 19 (M.W. 250,000) and S-97 Pharmaceutical Grade (M.W. 70,000), of GAF Chemicals Corporation.

Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1 103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalkane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid, incorporated herein by reference.

Another useful class of polymeric agents includes polyamino acids, particularly those containing proportions of anionic surface-active amino acids such as aspartic acid, glutamic acid and phosphoserine, as disclosed in U.S. Pat. No. 4,866,161 Sikes et al., incorporated herein by reference.

In preparing oral care compositions, it is sometimes necessary to add some thickening material to provide a desirable consistency or to stabilize or enhance the performance of the formulation. In certain embodiments, the thickening agents are carboxyvinyl polymers, carrageenan, xanthan gum, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of about 0.5% to about 5.0% by weight of the total composition are used.

Abrasives

Natural calcium carbonate is found in rocks such as chalk, limestone, marble and travertine. It is also the principle component of egg shells and the shells of mollusks. The natural calcium carbonate abrasive of the invention is typically a finely ground limestone which may optionally be refined or partially refined to remove impurities. For use in the present invention, the material has an average particle size of less than 10 microns, e.g., 3-7 microns, e.g. about 5.5 microns. For example, a small particle silica may have an average particle size (D50) of 2.5-4.5 microns. Because natural calcium carbonate may contain a high proportion of relatively large particles of not carefully controlled, which may unacceptably increase the abrasivity, preferably no more than 0.01%, preferably no more than 0.004% by weight of particles would not pass through a 325 mesh. The material has strong crystal structure, and is thus much harder and more abrasive than precipitated calcium carbonate. The tap density for the natural calcium carbonate is for example between 1 and 1.5 g/cc, e.g., about 1.2 for example about 1.19 g/cc. There are different polymorphs of natural calcium carbonate, e.g., calcite, aragonite and vaterite, calcite being preferred for purposes of this invention. An example of a commercially available product suitable for use in the present invention includes Vicron® 25-11 FG from GMZ.

Precipitated calcium carbonate is generally made by calcining limestone, to make calcium oxide (lime), which can then be converted back to calcium carbonate by reaction with carbon dioxide in water. Precipitated calcium carbonate has a different crystal structure from natural calcium carbonate. It is generally more friable and more porous, thus having lower abrasivity and higher water absorption. For use in the present invention, the particles are small, e.g., having an average particle size of 1-5 microns, and e.g., no more than 0.1%, preferably no more than 0.05% by weight of particles which would not pass through a 325 mesh. The particles may for example have a D50 of 3-6 microns, for example 3.8=4.9, e.g., about 4.3; a D50 of 1-4 microns, e.g. 2.2-2.6 microns, e.g., about 2.4 microns, and a D10 of 1-2 microns, e.g., 1.2-1.4, e.g. about 1.3 microns. The particles have relatively high water absorption, e.g., at least 25 g/100 g, e.g. 30-70 g/100 g. Examples of commercially available products suitable for use in the present invention include, for example, Carbolag® 15 Plus from Lagos Industria Quimica.

In certain embodiments the invention may comprise additional calcium-containing abrasives, for example calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4 \cdot 2H_2O$, also sometimes referred to herein as DiCal) or calcium pyrophosphate, and/or silica abrasives, sodium metaphosphate, potassium metaphosphate, aluminum silicate, calcined alumina, bentonite or other siliceous materials, or combinations thereof. Any silica suitable for oral care compositions may be used, such as precipitated silicas or silica gels. For example synthetic amorphous silica. Silica may also be available as a thickening agent, e.g., particle silica. For example, the silica can also be small particle silica (e.g., Sorbosil AC43 from PQ Corporation, Warrington, United Kingdom). However the additional abrasives are preferably not present in a type or amount so as to increase the RDA of the dentifrice to levels which could damage sensitive teeth, e.g., greater than 130.

Water

Water is present in the oral compositions of the invention. Water, employed in the preparation of commercial oral compositions should be deionized and free of organic impurities. Water commonly makes up the balance of the compositions and includes 5% to 45%, e.g., 10% to 20%, e.g., 25-35%, by weight of the oral compositions. This amount of water includes the free water which is added plus that amount which is introduced with other materials such as with sorbitol or silica or any components of the invention. The Karl Fischer method is a one measure of calculating free water.

Humectants

Within certain embodiments of the oral compositions, it is also desirable to incorporate a further humectant (e.g., in addition to glycerin) to reduce evaporation and also contribute towards preservation by lowering water activity. Certain humectants can also impart desirable sweetness or flavor to the compositions. The humectant, on a pure humectant basis, generally includes 15% to 70% in one embodiment or 30% to 65% in another embodiment by weight of the composition.

Suitable humectants include edible polyhydric alcohols such as glycerin, sorbitol, xylitol, propylene glycol as well as other polyols and mixtures of these humectants. Mixtures of glycerine and sorbitol may be used in certain embodiments as the humectant component of the compositions herein (e.g., Composition 1.0 et seq).

The present invention in its method aspect involves applying to the oral cavity a safe and effective amount of the compositions described herein.

The compositions and methods according to the invention (e.g., Composition 1.0 et seq) can be incorporated into oral compositions for the care of the mouth and teeth such as toothpastes, transparent pastes, gels, mouth rinses, sprays and chewing gum.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. It is understood that when formulations are described, they may be described in terms of their ingredients, as is common in the art, notwithstanding that these ingredients may react with one another in the actual formulation as it is made, stored and used, and such products are intended to be covered by the formulations described.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

EXAMPLES

Aqueous solutions containing arginine and zinc salts were created to carry out the following Examples. Solution 1 was prepared by mixing L-arginine (0.375 g), zinc oxide (ZnO, 0.25 g), and zinc citrate trihydrate (0.125 g) in deionized water (24.25 mL). These values correspond to the following percentages by mass: 1.5% L-arginine, 1% ZnO, 0.5% zinc citrate trihydrate. Additional control solutions were prepared of each regent alone at equal concentrations. Simple solution preparation is summarized in Table 1. Each solution was diluted to 25 g total mass with deionized water.

TABLE 1

Preparation scheme of Solutions containing Zinc Salts/Arginine and Controls

| Simple Solution | Reagent | Amount (g) | Mass Percent |
|---|---|---|---|
| Zinc Oxide/Zinc Citrate/Arginine | L-arginine | 0.375 | 1.5% |
|  | ZnO | 0.25 | 1.0% |
|  | Zinc Citrate Trihydrate | 0.125 | 0.5% |
| Arginine | L-arginine | 0.375 | 1.5% |
| Zinc Oxide | ZnO | 0.250 | 1.0% |
| Zinc Citrate | Zinc Citrate Trihydrate | 0.125 | 0.5% |

Example 1—Test for Buffering Effect of Zinc Oxide/Zinc Citrate/Arginine Solution Following Acid Challenge with Cola Beverage Paraffin-stimulated whole saliva was collected from a healthy subject. Each saliva sample was mixed by an appropriate means. Immediately prior to analysis, the ex-vivo saliva samples were pretreated with aliquots of Solution 1 to give a range of active dilutions. A control sample containing untreated whole saliva was also prepared for comparison. The dilutions were prepared as in Table 2.

TABLE 2

Concentrations of zinc oxide/zinc citrate/arginine treated saliva.

| Sample | Zinc Oxide/Zinc Citrate/Arginine Stock (mL) | Whole Saliva (mL) | % Zinc Oxide/Zinc Citrate/Arginine Solution |
|---|---|---|---|
| 1 | 0.00 | 4.000 | 0.000 |
| 2 | 0.100 | 3.900 | 0.025 |
| 3 | 0.250 | 3.750 | 0.0625 |
| 4 | 0.500 | 3.500 | 0.1250 |

The samples as described in Table 2 were tested for buffering effect on the pH of saliva following acid challenge with a cola beverage. Initial pH values of the treated samples were obtained. A cola beverage (1 mL) was added to the saliva sample. The resultant was mixed for 30 seconds at room temperature at the conclusion of which the pH of the sample was recorded. This process was repeated step-wise up to a total of 40 mL of cola. The results are shown in FIG. 1. As shown, increasing concentrations of zinc oxide/zinc citrate/arginine alkaline shifted the isoelectric point of the saliva enhancing buffering capacity. Solutions having zinc oxide/zinc citrate/arginine showed strong buffering effects at each concentration measured. However, the results show that as the concentration of zinc oxide/zinc citrate/arginine increases, the buffering effect on the saliva also increases.

Similar tests were carried out to compare the buffering effect against cola of control solutions containing L-arginine/zinc oxide/zinc citrate as summarized below in Table 3.

TABLE 3

Concentrations of zinc oxide/zinc citrate/arginine
treated saliva in comparison with controls.

| Sample | Reagent (mL) | Whole Saliva (mL) | % Reagent in Solution |
|---|---|---|---|
| 1 | Zinc Oxide/Zinc Citrate/arginine (.250) | 3.750 | 0.0625 |
| 2 | L-Arginine (.250) | 3.750 | 0.0625 |
| 3 | Zinc Oxide/Zinc Citrate (.250) | 3.750 | 0.0625 |
| 4 | Zinc Oxide (.250) | 3.750 | 0.0625 |
| 5 | Zinc Citrate (.250) | 3.750 | 0.0625 |

Figure 2:
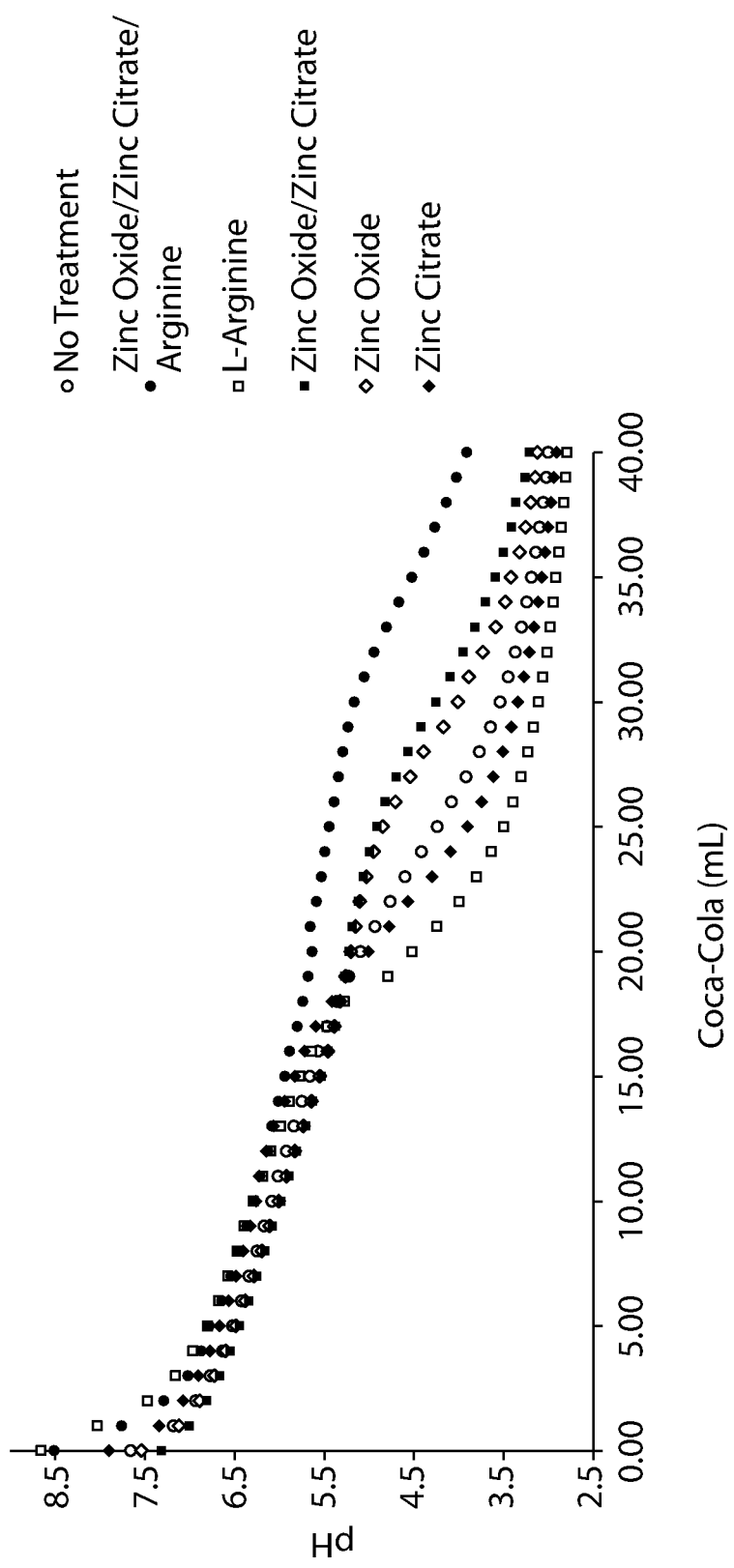
FIG. 2 illustrates the pH of whole saliva treated with zinc oxide/zinc citrate/arginine solutions before and after acid challenge with a cola beverage as a function of volume of cola added to the solution in comparison with control solutions.

The titrations with the same cola beverage were repeated in presence of saliva treated with the aforementioned zinc oxide/zinc citrate/arginine controls (i.e., Samples 2-5 in Table 3). The concentration of each reagent in control Samples 2-5 were held constant in comparison to the 0.0625% zinc oxide/zinc citrate/arginine simple solution. Therefore, direct comparison of any effect could be made by each control solution to zinc oxide/zinc citrate/arginine. As shown in FIG. 2, zinc oxide/zinc citrate/arginine out performs all control solutions at equal concentration of active agents. The zinc oxide/zinc citrate/arginine solution showed much better ability to buffer the acidic cola beverage than the control samples. The isoelectric point of zinc oxide/zinc citrate/arginine is alkaline shifted more than 5 mL in comparison to a zinc oxide/zinc citrate and a zinc oxide solution. Zinc citrate and arginine conversely acid shifted the isoelectric point in comparison to the untreated sample providing no acid neutralization benefit.

Figure 3:
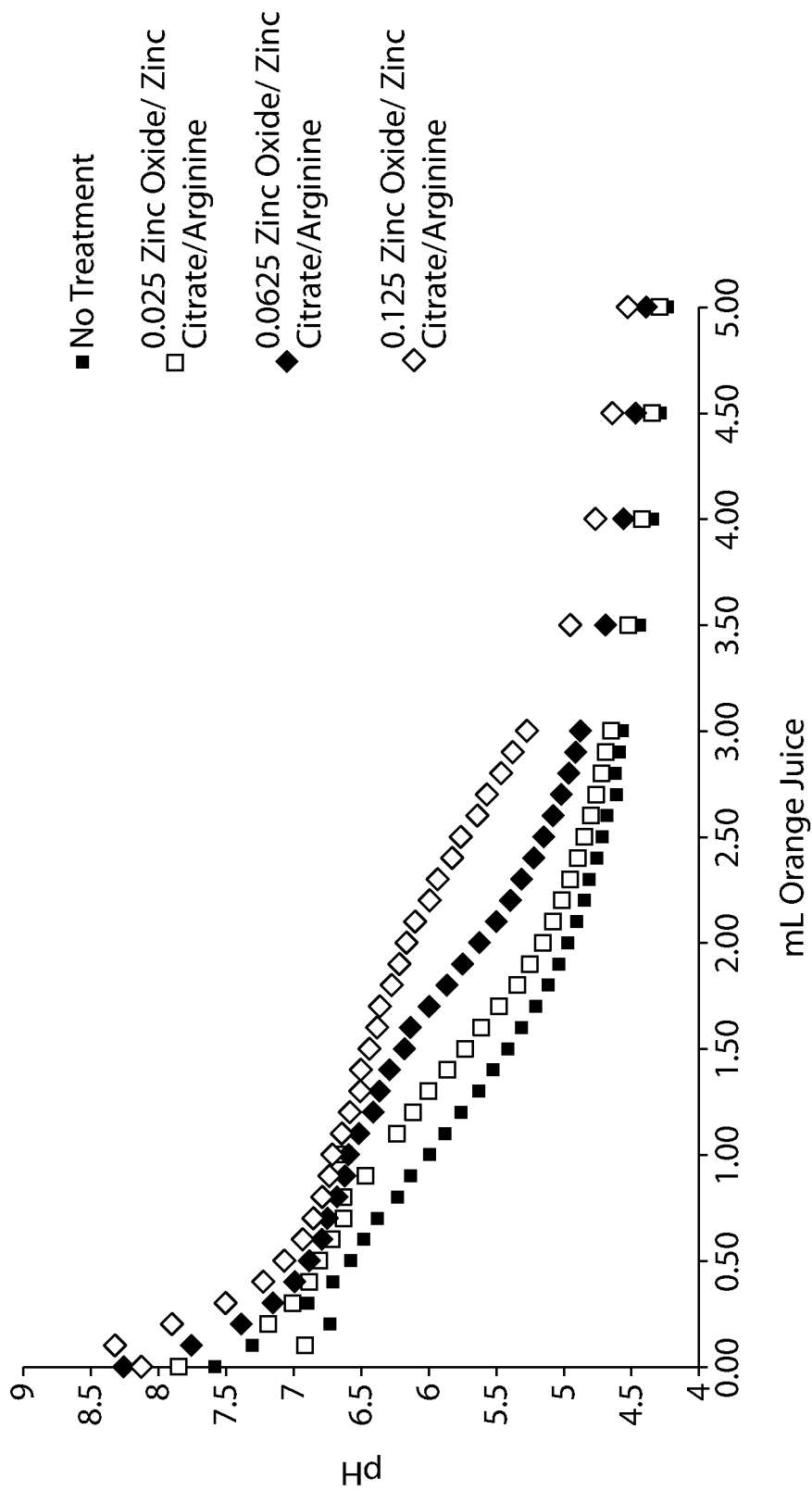
FIG. 3 illustrates the pH of whole saliva treated with zinc oxide/zinc citrate/arginine solutions before and after acid challenge with orange juice as a function of volume of orange juice added to the solution, where the solutions having varying concentrations of zinc oxide/zinc citrate/arginine.

Example 2—Test for Buffering Effect of Zinc Oxide/Zinc Citrate/Arginine Solution Following Acid Challenge with Orange Juice Four solutions containing whole saliva and zinc oxide/zinc citrate/arginine at varying proportions were prepared in accordance with the methods laid out in Example 1 above. The solutions contained the same concentrations as Samples 1-4 as defined in Table 2. The samples were tested for buffering effect on the pH of saliva following acid challenge with orange juice. Initial pH values of the treated samples were obtained. Orange juice (0.1 mL) was added to the saliva sample. The resultant was mixed for 30 seconds at room temperature at the conclusion of which the pH of the sample was recorded. This process was repeated step-wise up to a total of 3.0 mL of orange juice. After this point, orange juice was added to the samples in an amount of 0.5 mL up to 5.0 mL. The results are shown in FIG. 3. As shown, increasing concentrations of zinc oxide/zinc citrate/arginine alkaline shifted the isoelectric point of the saliva enhancing buffering capacity. Zinc oxide/zinc citrate/arginine solutions showed strong buffering effects at each concentration measured. However, the results show that as the concentration of zinc oxide/zinc citrate/arginine increases, the buffering effect on the saliva also increases, especially at moderate amounts of orange juice (i.e., between 2 and 3 mL).

Figure 4:
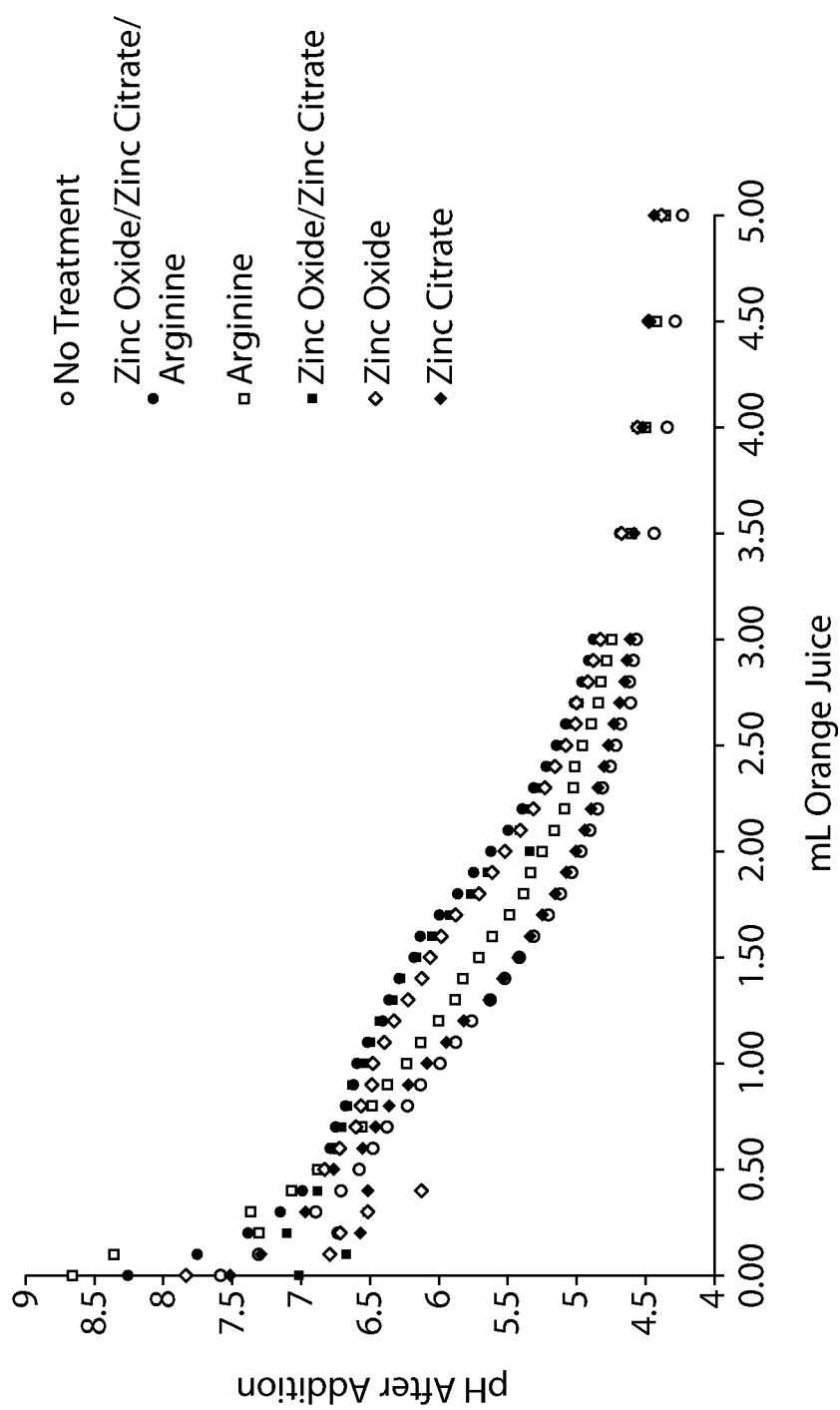
FIG. 4 illustrates the pH of whole saliva treated with zinc oxide/zinc citrate/arginine solutions before and after acid challenge with orange juice as a function of volume of orange juice added to the solution in comparison with control solutions.

Similar tests as those in Example 1 were carried out to compare the buffering effect against orange juice of solutions containing L-arginine/zinc oxide/zinc citrate with control solutions as summarized above in Table 3. The titrations with the same orange juice were repeated in presence of saliva treated with controls (i.e., Samples 2-5 in Table 3). The concentration of each reagent in control Samples 2-5 were held constant in comparison to the 0.0625% zinc oxide/zinc citrate/arginine simple solution. As shown in FIG. 4, the zinc oxide/zinc citrate/arginine solution showed an ability to buffer the acidic orange juice beverage better than or on par with the control samples. The isoelectric point of zinc oxide/zinc citrate/arginine is comparable to that of the zinc oxide/zinc citrate and zinc oxide solution. Zinc citrate alone showed no benefit in comparison the untreated control.

Taken together, the data clearly demonstrate the role of zinc oxide/zinc citrate/arginine in enhancing the resistance of saliva to acidic beverages. The data suggest the complex of L-arginine/zinc oxide/zinc citrate, not the entities thereof (arginine, zinc), are required for buffering effect.

Example 3—Test for Buffering Effect of Zinc Oxide/Zinc Citrate/Arginine Solution Following Acid Challenge with Hydrochloric Acid Paraffin-stimulated whole saliva was collected from three healthy subjects (Donors 1-3). Each saliva sample was mixed by ordinary means in the art. Immediately prior to analysis, the ex-vivo saliva samples were pretreated with aliquots of the simple solutions to give a range of active dilutions (i.e., total $Zn^{2+}$ concentration of about 0-1500 ppm) including an untreated control. The concentrations of actives (i.e., zinc oxide/zinc citrate/arginine, L-arginine, zinc oxide, zinc citrate) were varied between 0.0% to 50% across all samples, as shown in FIGS. 5-10.

An initial pH of the treated sample was obtained. Dilute hydrochloric acid (HCl, 0.01 M, 6 mL) was added to each saliva sample. The resultant was mixed for 20 minutes at room temperature. The pH of the sample was recorded at the conclusion of the reaction time. Zinc concentration in each sample was determined by ICP-AES. The results are summarized in FIGS. 5-10.

Figure 5:
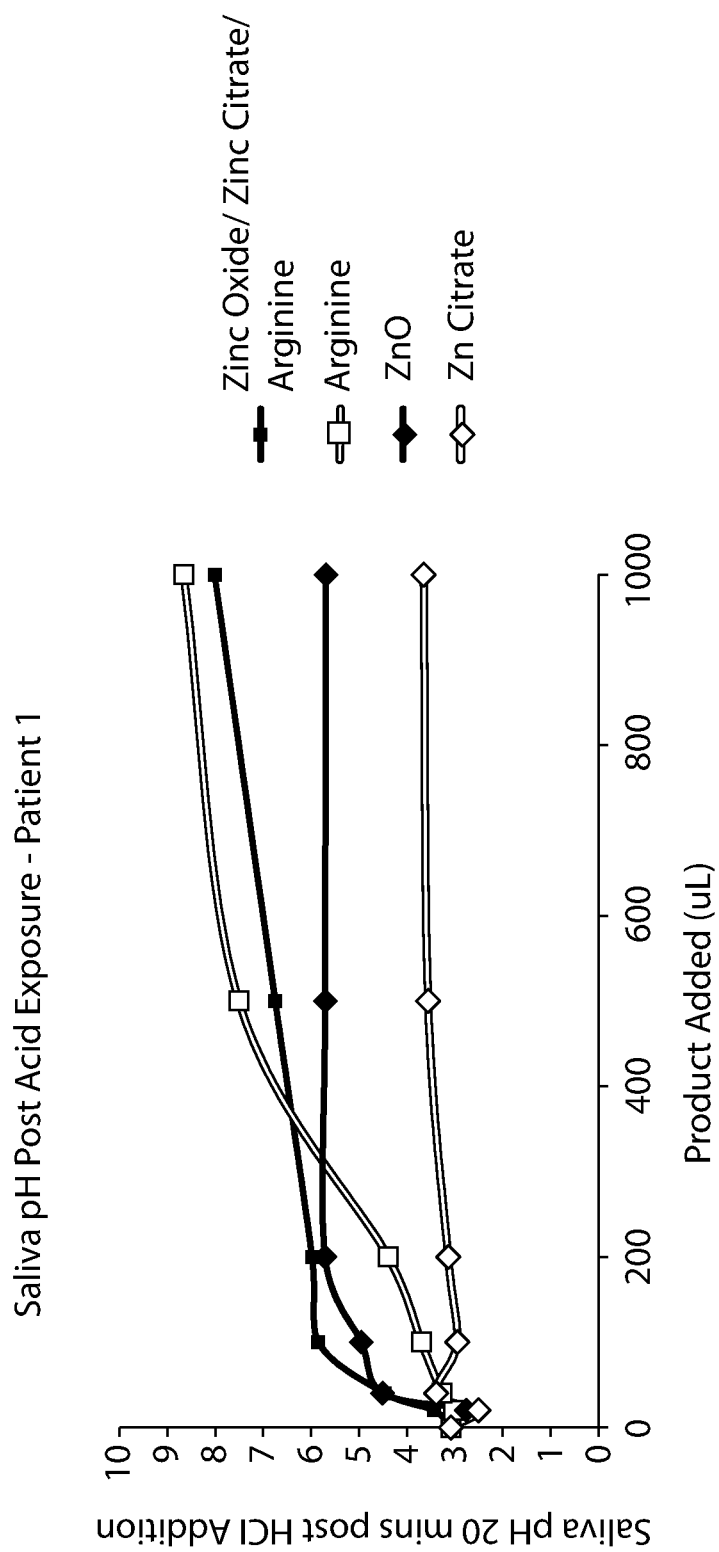
FIG. 5 illustrates the pH of whole saliva from a donor (Donor 1) treated with zinc oxide/zinc citrate/arginine solutions after acid challenge with a dilute hydrochloric acid as a function of reagent added to the solution in comparison with control solutions.
Figure 6:
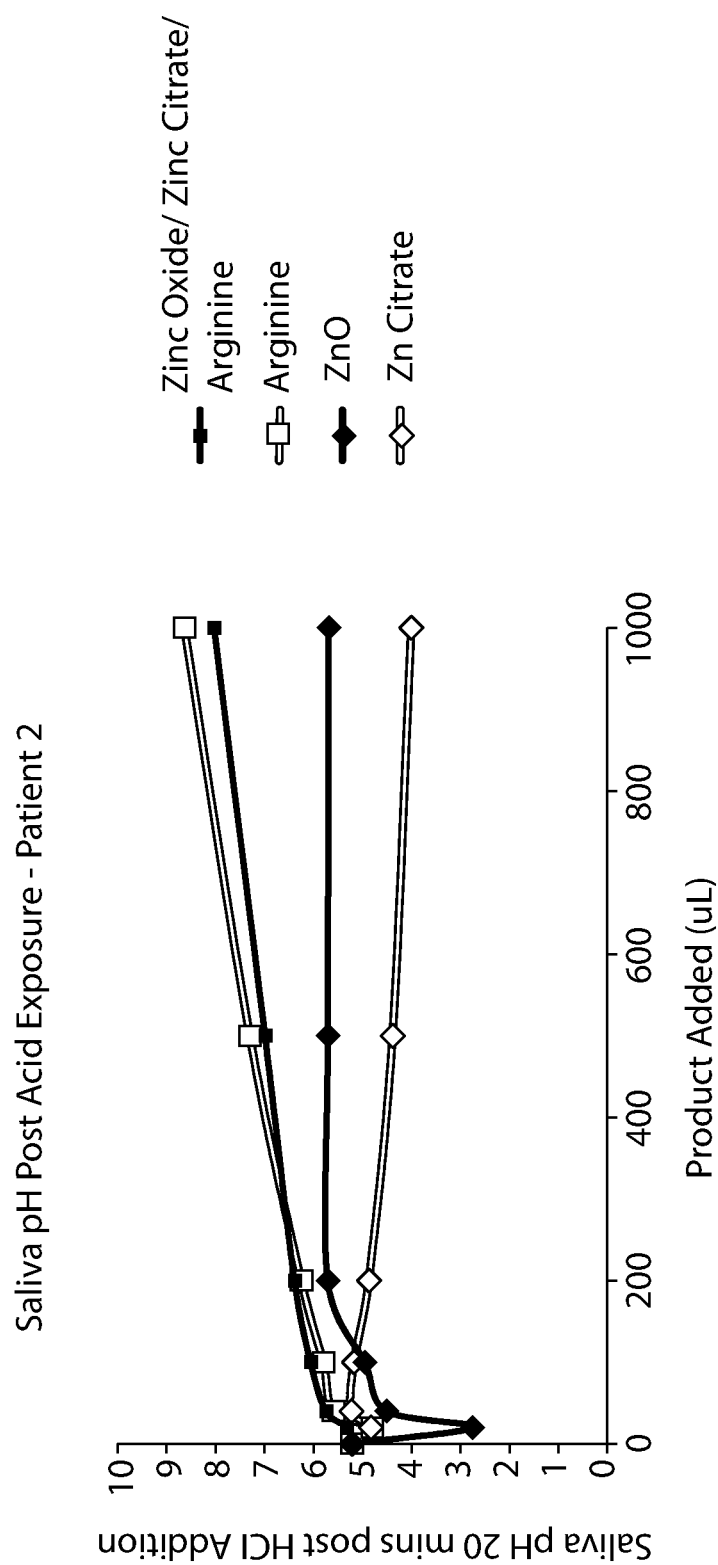
FIG. 6 illustrates the pH of whole saliva from a donor (Donor 2) treated with zinc oxide/zinc citrate/arginine solutions after acid challenge with a dilute hydrochloric acid as a function of reagent added to the solution in comparison with control solutions.
Figure 7:
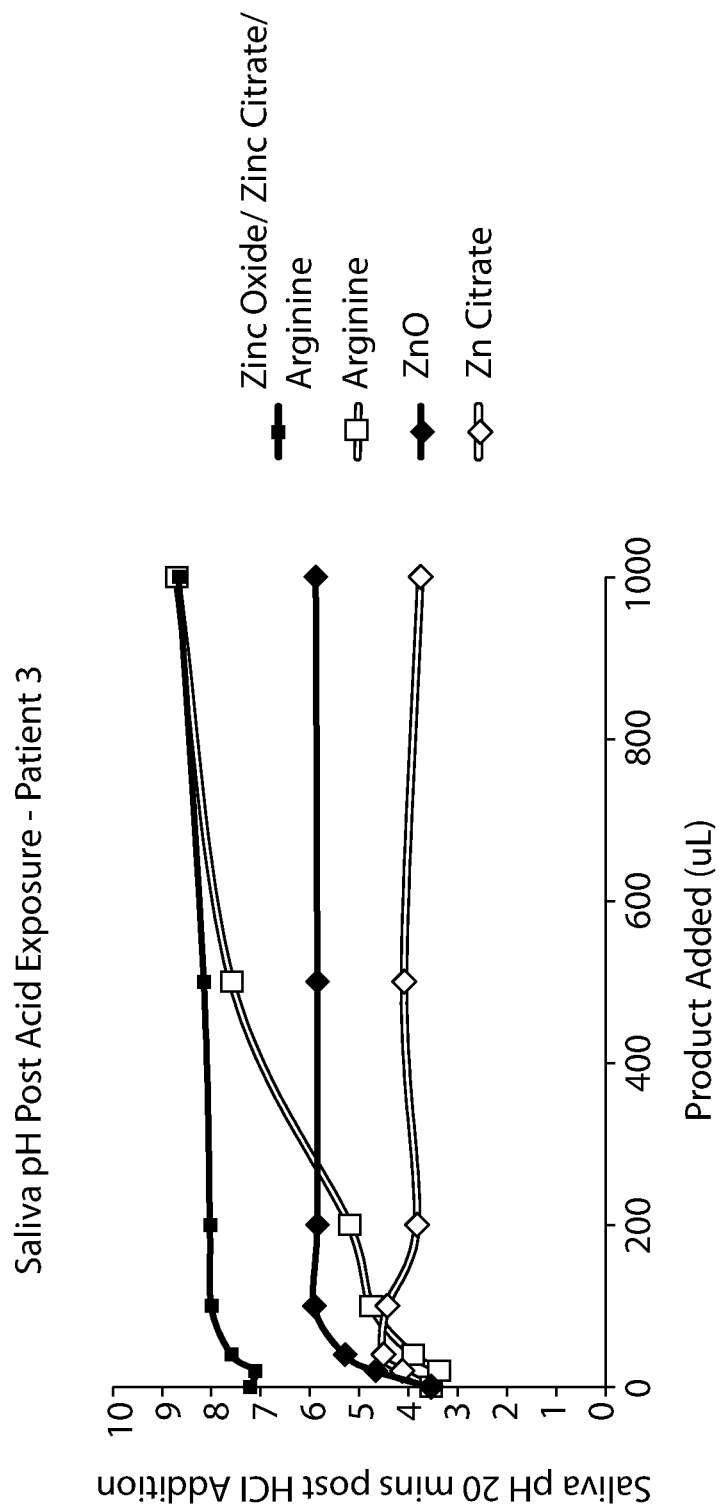
FIG. 7 illustrates the pH of whole saliva from a donor (Donor 3) treated with zinc oxide/zinc citrate/arginine solutions after acid challenge with a dilute hydrochloric acid as a function of reagent added to the solution in comparison with control solutions.

FIGS. 5-7 show the superior acid buffering effects of even small amounts of zinc oxide/zinc citrate/arginine over subsequent control solutions. the results indicate that the combination of zinc and L-arginine boosts the acid buffering capacity of saliva over the L-arginine control. Surprisingly, this augmentation (up to 2 pH log units) is most evident in individuals with low salivary buffering capacity (Donor #1 and Donor #3) at very low amounts of treatment (<0.200 For example, FIGS. 5-7 each show that the samples having 200 μL or less zinc oxide/zinc citrate/arginine showed much better buffering of the acid solutions than each of the arginine, zinc oxide or zinc citrate solutions at the same concentrations. The same figures show that only solutions containing very high amounts of L-arginine (>500 μL) were able to match this effect. Zinc oxide provided some pH stabilization in treated samples upon acid exposure. However, this effect was quickly exhausted, not showing a dose response above 0.1% treatment. Furthermore, the overall pH of the saliva after acid exposure was lower in saliva treated with ZnO than zinc oxide/zinc citrate/arginine treated saliva. This leads to a larger change in pH upon acid exposure in ZnO samples, decreasing benefits on this active in comparison to zinc oxide/zinc citrate/arginine. In all donors, zinc citrate provided little to no buffering effect at all, dropping the pH of all treated samples below 4.0.

Example 4—Test for Buffering Effect of Zinc Oxide/Zinc Citrate/Arginine Solution Following Sucrose Challenge Paraffin-stimulated whole saliva was collected from three healthy subjects (Donors A-C). Each saliva sample was mixed by ordinary means in the art. Prior to analysis, the ex-vivo saliva samples were pretreated with aliquots of the simple solutions to give a range of active dilutions (i.e., total $Zn^{2+}$ concentration of about 0-3000 ppm) including an untreated control in order to test for buffering effect against sucrose challenge as a function of zinc concentration. An initial pH of the treated sample was obtained. A sucrose solution (5%, 1 mL) was added to each saliva sample. The resultant was mixed for and then incubated at 37° C. and the pH was monitored at 2 hours, 4 hours, 6 hours, and overnight. Zinc concentration in each sample was determined by ICP-AES.

Figure 8:
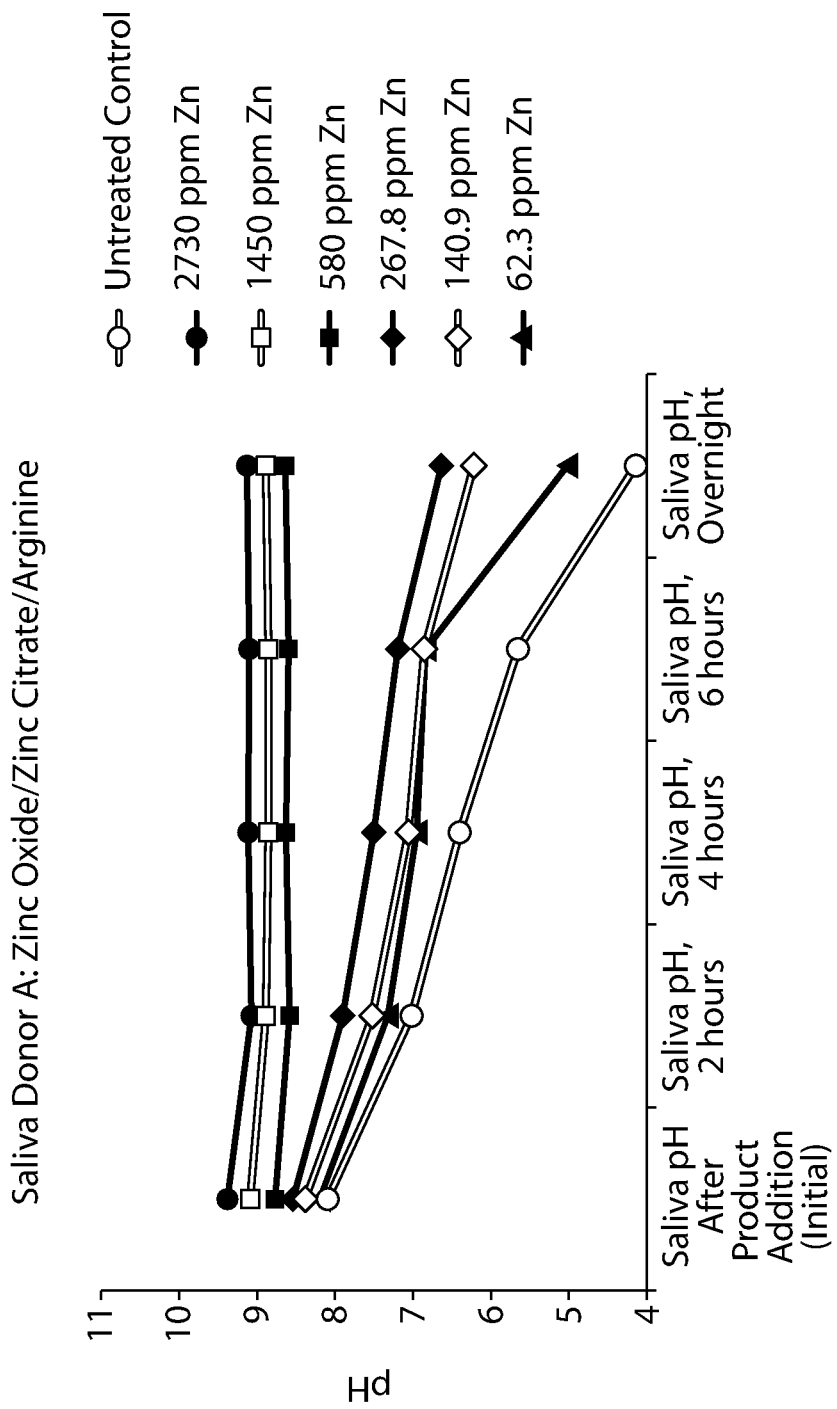
FIG. 8 illustrates the pH of whole saliva from a donor (Donor A) treated with zinc oxide/zinc citrate/arginine solutions having various concentrations of zinc ion as a function of time.
Figure 9:
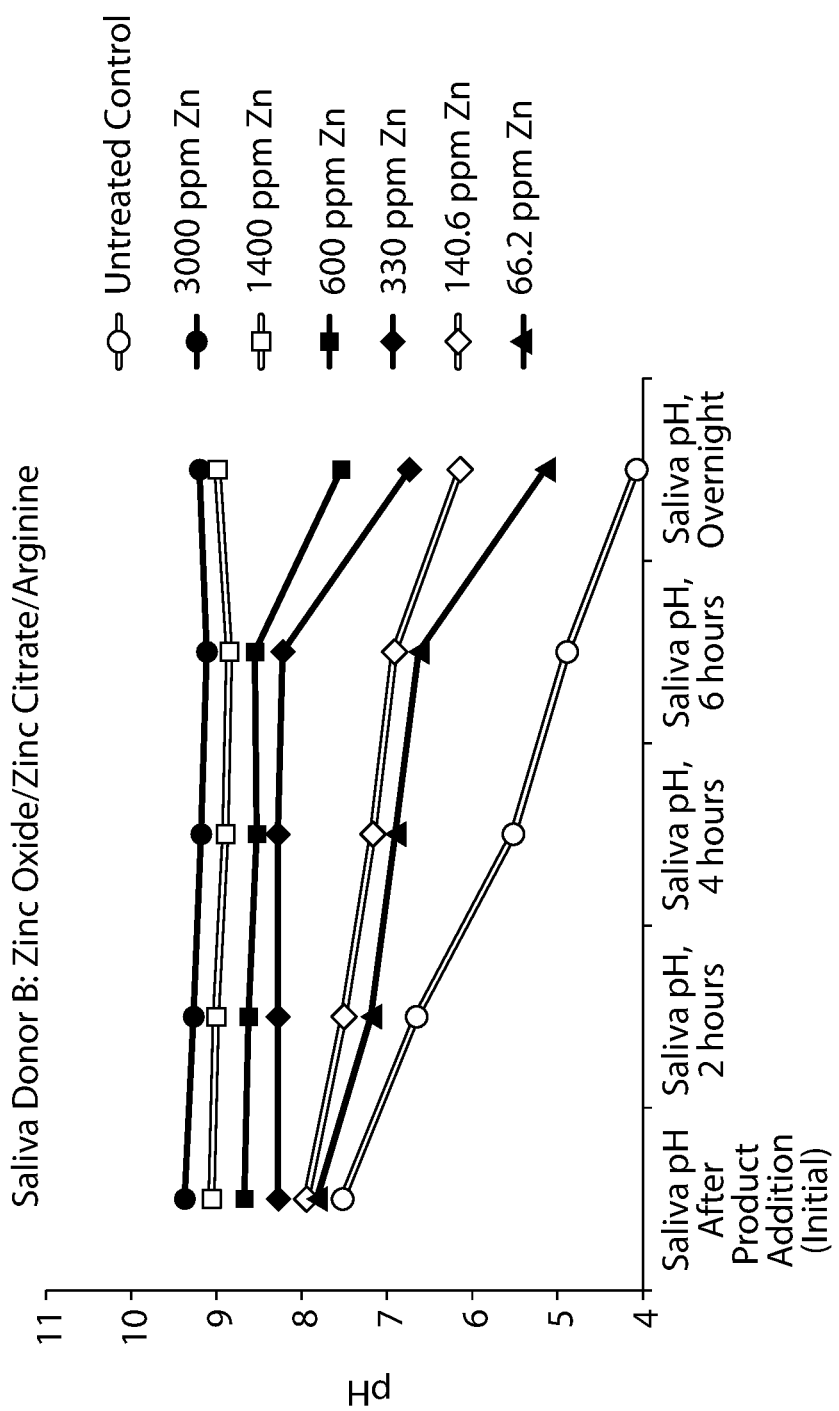
FIG. 9 illustrates the pH of whole saliva from a donor (Donor B) treated with zinc oxide/zinc citrate/arginine solutions having various concentrations of zinc ion as a function of time.
Figure 10:
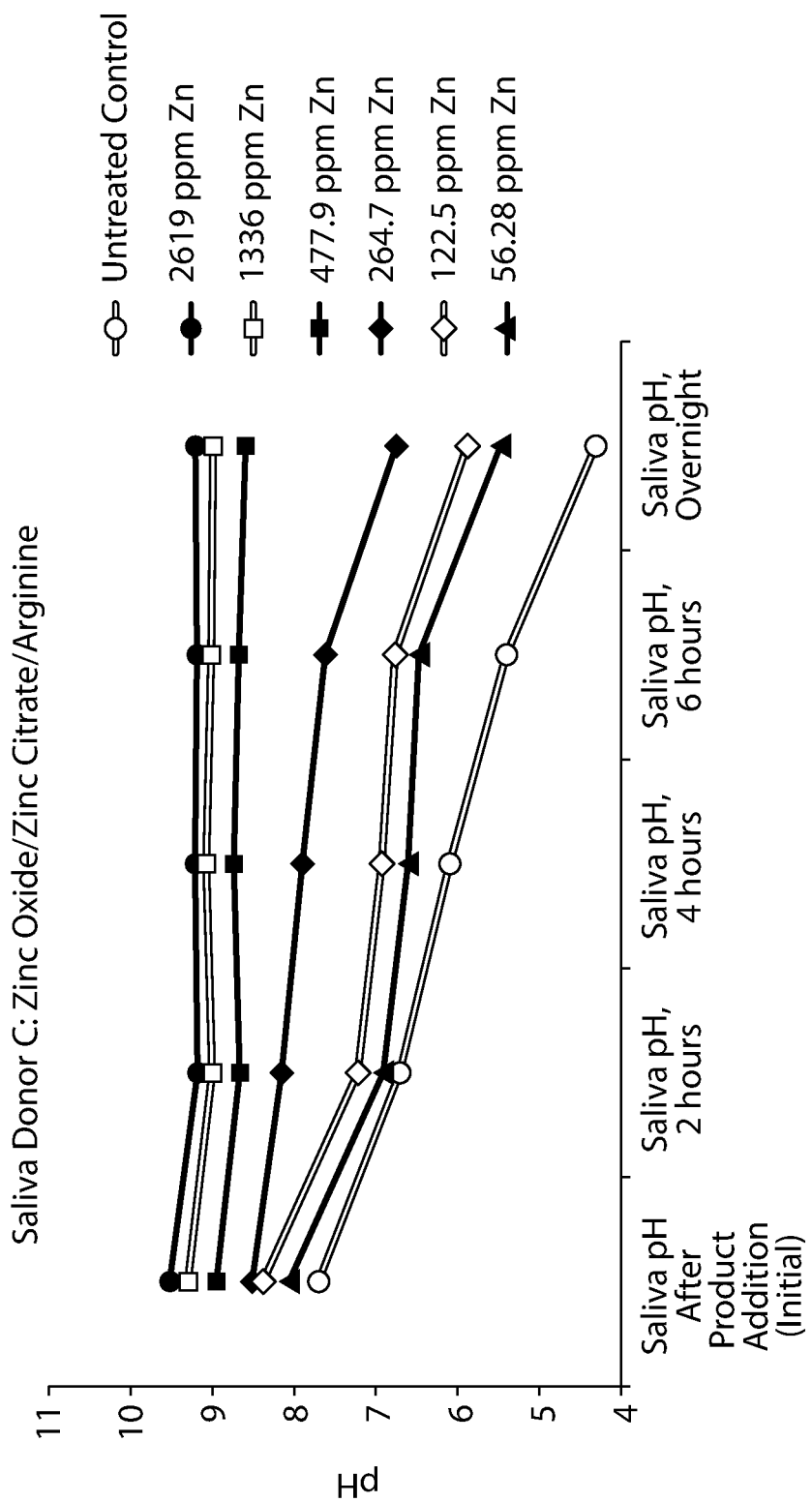
FIG. 10 illustrates the pH of whole saliva from a donor (Donor C) treated with zinc oxide/zinc citrate/arginine solutions having various concentrations of zinc ion as a function of time.

Charts showing the pH of the saliva of each donor pre- and post-sucrose challenge as a function of zinc (i.e., in zinc oxide/zinc citrate/arginine solutions) concentration and time are shown in FIGS. 8-10. The control sample of each donor saliva shows a steady drop as a function of time consistent with unregulated acid production by oral bacteria. However, upon adding zinc oxide/zinc citrate/arginine, the effect on pH dropping is greatly attenuated, even at smaller concentrations of zinc.

With specific reference to FIG. 8, solutions containing concentrations of at least about 580 ppm $Zn^{2+}$ showed a stable buffering effect across the entire testing period. FIG. 10 shows similar results for solutions containing concentrations of at least about 478 ppm $Zn^{2+}$. FIG. 9 shows that concentrations above 600 ppm $Zn^{2+}$ (i.e., 1400 and 3000 ppm) exhibit stable saliva buffering across the entire testing period, while the solution containing 600 ppm $Zn^{2+}$ showed a slight drop in buffering effect after 6 hours. This buffering effect increases as the concentration of zinc ions increase in the composition.

Figure 11:
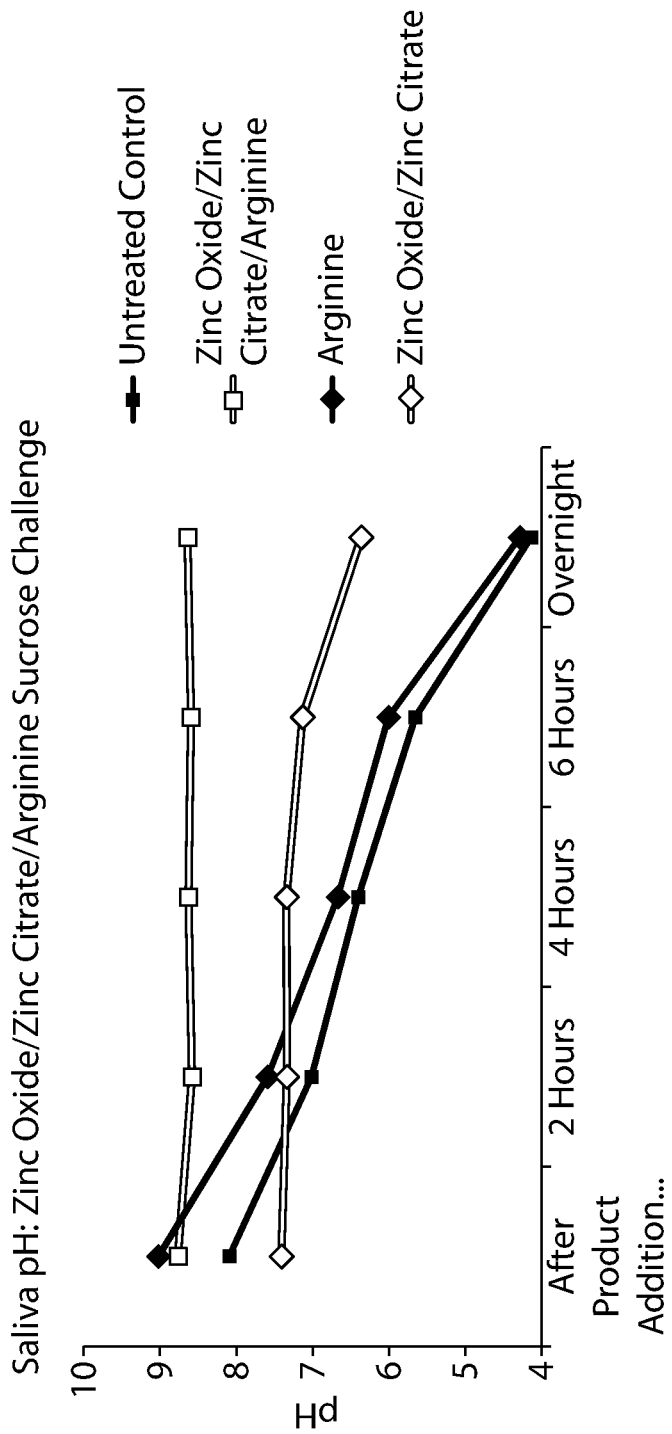
FIG. 11 illustrates the pH of whole saliva from a donor (Donor A) treated with zinc oxide/zinc citrate/arginine solutions after sucrose challenge as a function of time in comparison with control solutions.

Further experiments were conducted to ensure that zinc oxide/zinc citrate/arginine, not its constituent parts, was needed to achieve the buffering capacity improvement described. The solutions tested were prepared according to the specifications as laid out in Table 3 above. As seen by FIG. 11, zinc oxide/zinc citrate/arginine out performs its constituent controls in maintaining a stable pH in response to bacterial acid production.

Figure 12:
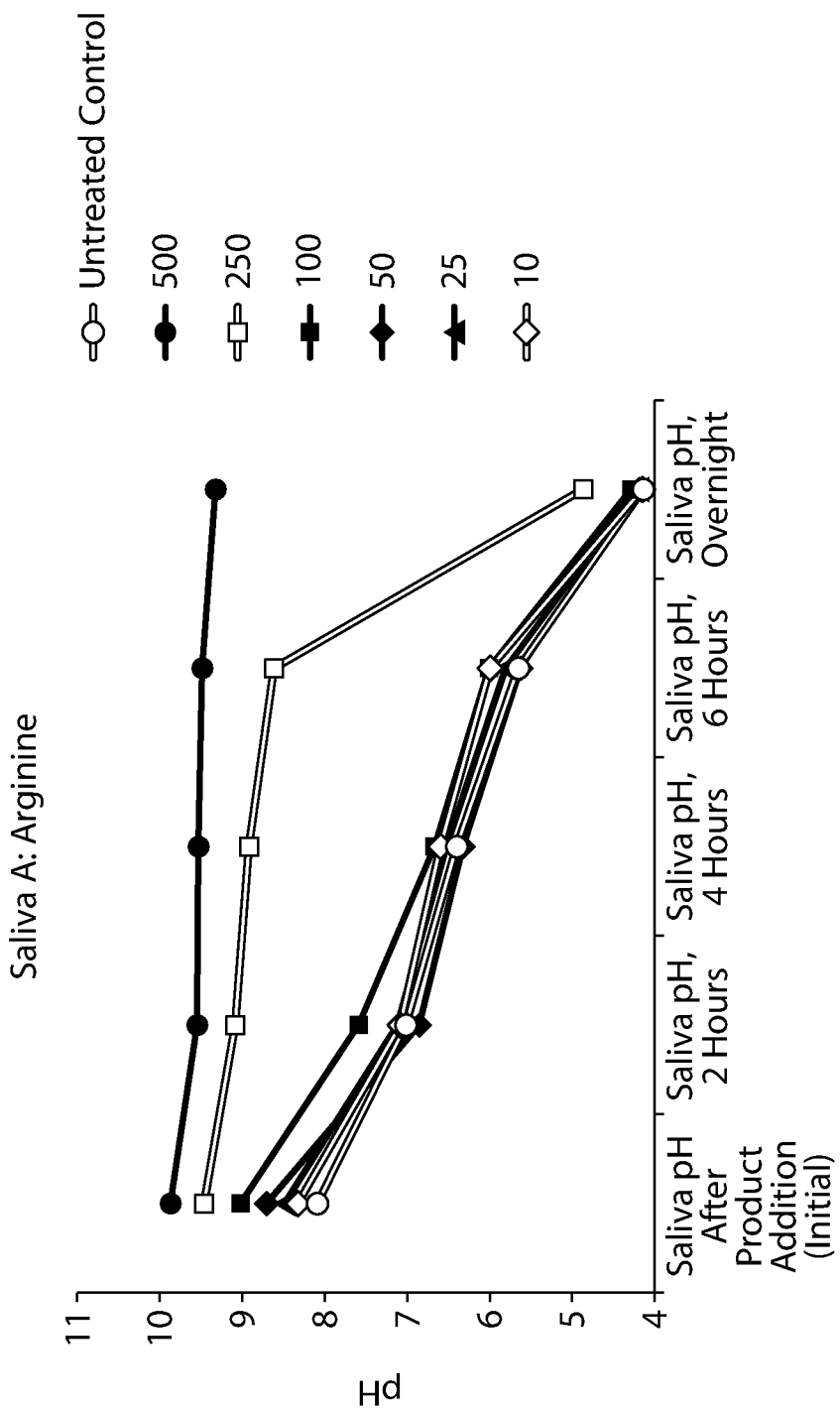
FIG. 12 illustrates the pH of whole saliva from a donor (Donor A) treated with arginine solutions having various concentrations of arginine after sucrose challenge as a function of time.
Figure 13:
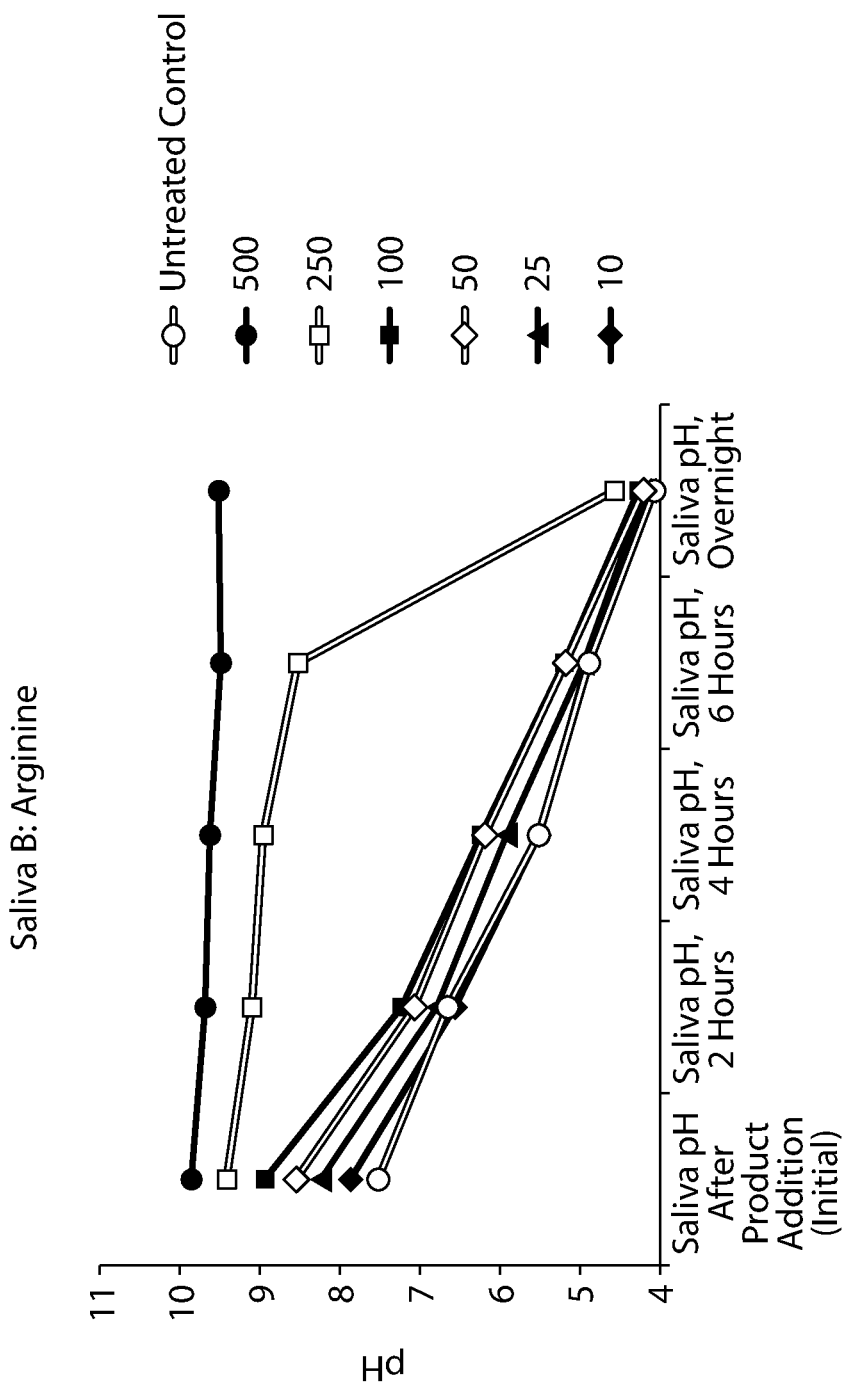
FIG. 13 illustrates the pH of whole saliva from a donor (Donor B) treated with arginine solutions having various concentrations of arginine after sucrose challenge as a function of time.
Figure 14:
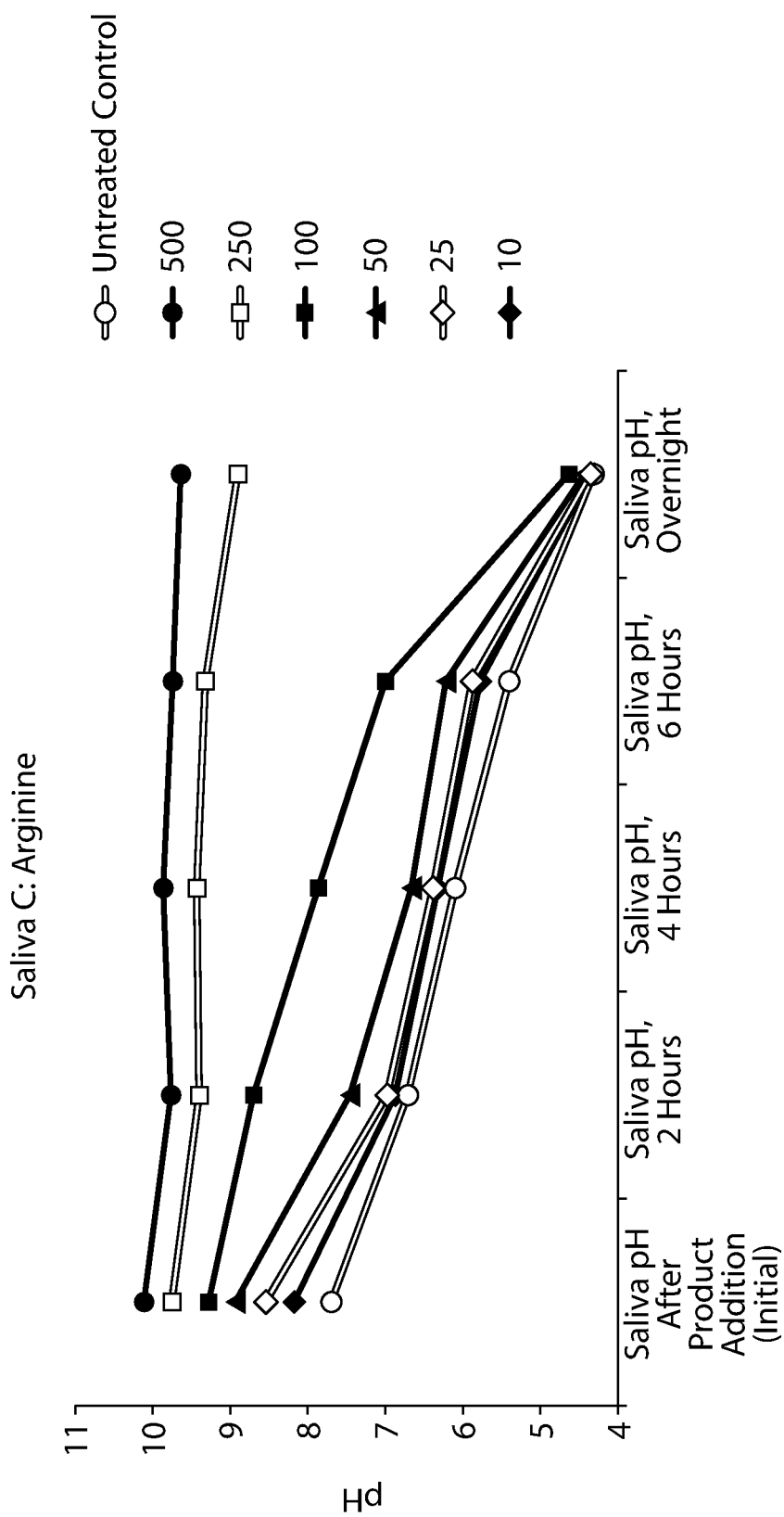
FIG. 14 illustrates the pH of whole saliva from a donor (Donor C) treated with arginine solutions having various concentrations of arginine after sucrose challenge as a function of time.

As shown in FIGS. 12-14, pH of the saliva from donors A-C were tested in sucrose challenged conditions as a function of arginine concentration. It is only at relatively high concentrations of arginine that any appreciable buffering effect is observed (i.e., 250 ppm to 500 ppm arginine). In donor C, modest buffering was observed with the 100 ppm arginine solution, but this effect was not seen in donors A or B.

Figure 15:
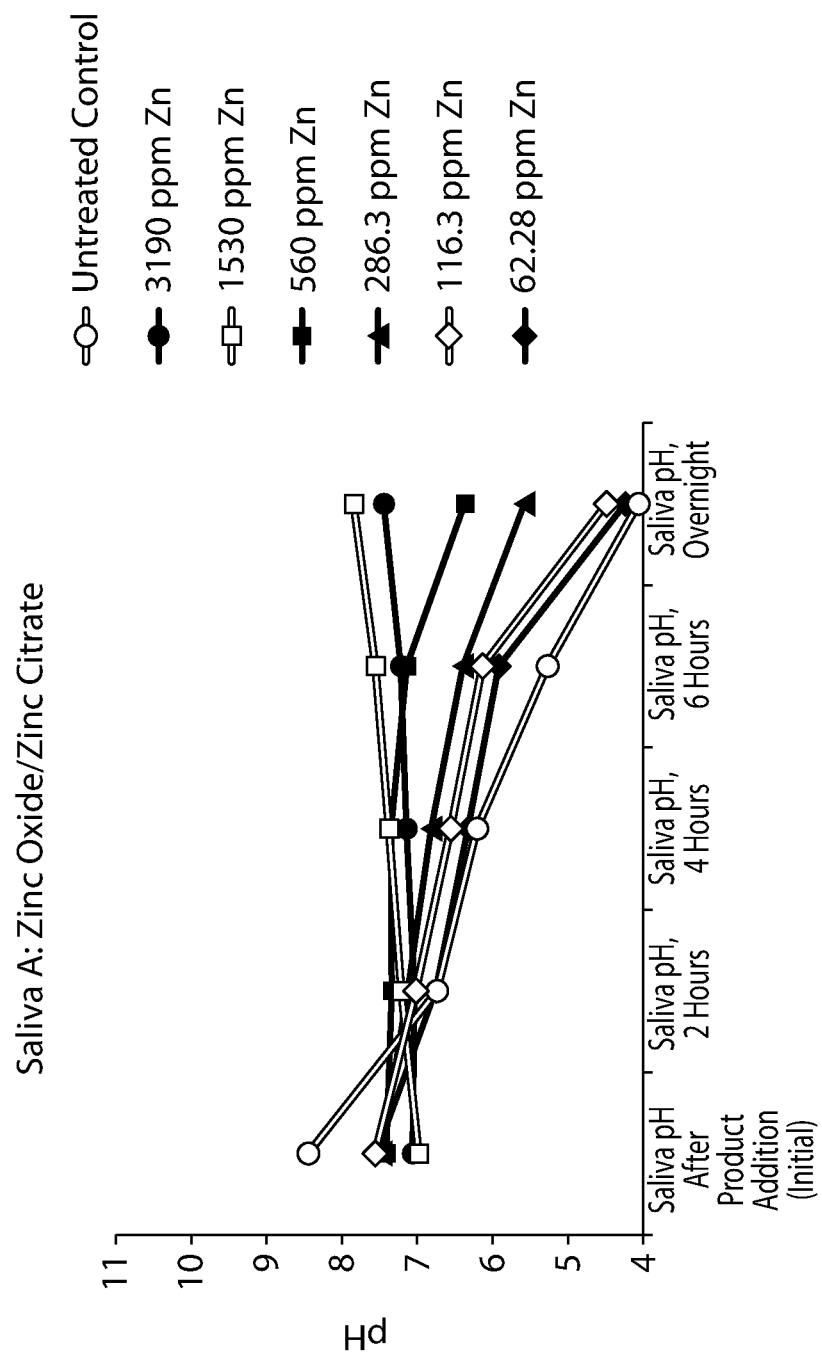
FIG. 15 illustrates the pH of whole saliva from a donor (Donor A) treated with zinc oxide/zinc citrate solutions having various concentrations of zinc oxide/zinc citrate after sucrose challenge as a function of time.
Figure 16:
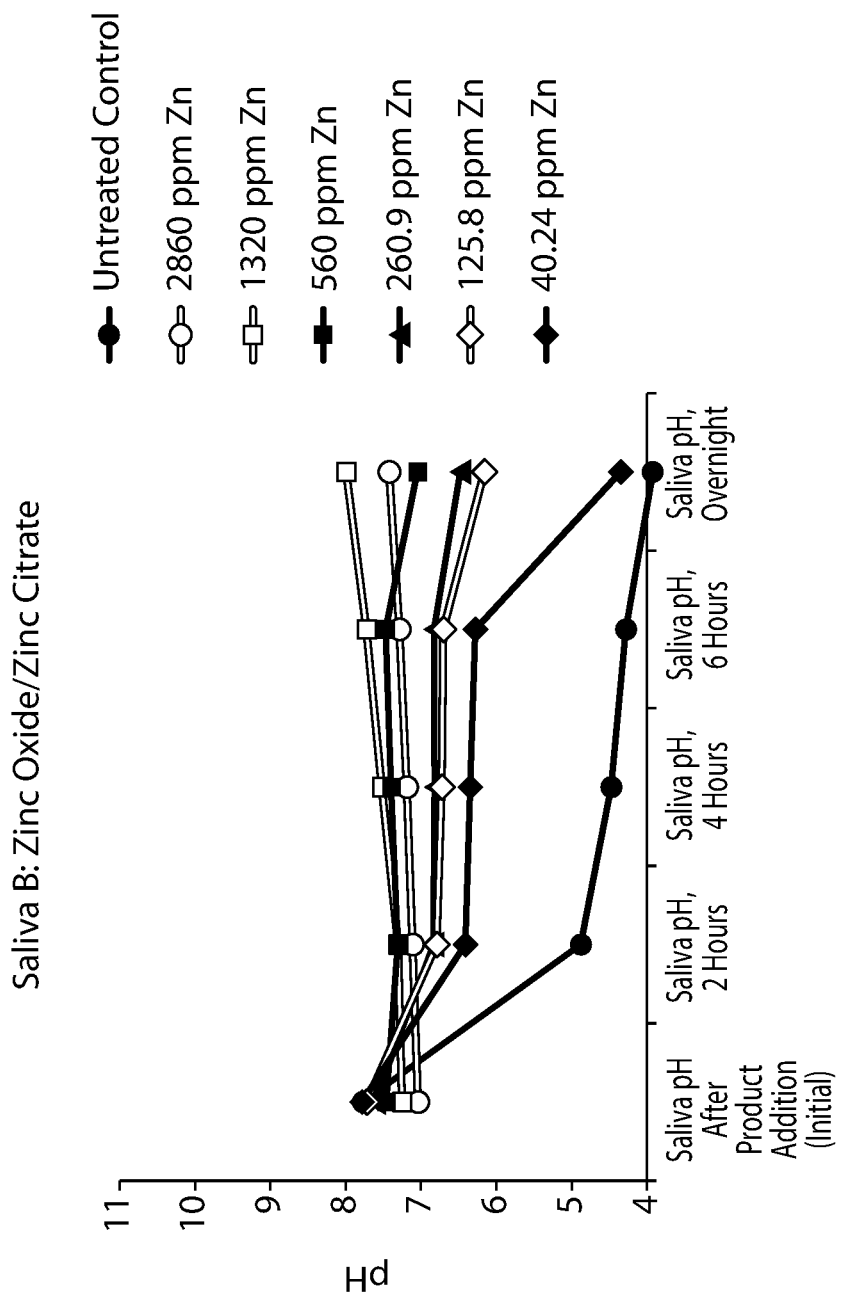
FIG. 16 illustrates the pH of whole saliva from a donor (Donor B) treated with zinc oxide/zinc citrate solutions having various concentrations of zinc oxide/zinc citrate after sucrose challenge as a function of time.
Figure 17:
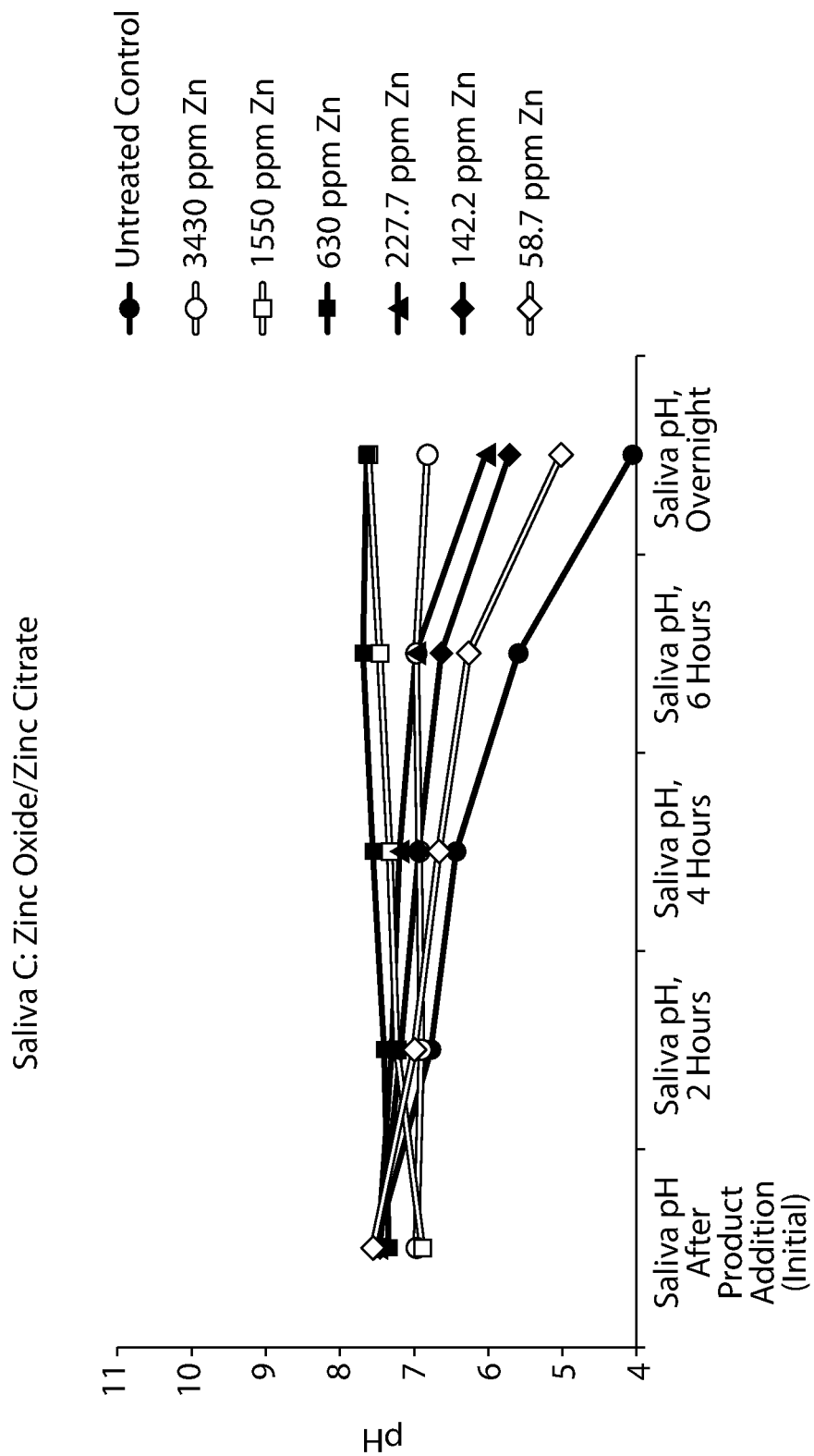
FIG. 17 illustrates the pH of whole saliva from a donor (Donor C) treated with zinc oxide/zinc citrate solutions having various concentrations of zinc oxide/zinc citrate after sucrose challenge as a function of time.

As shown in FIGS. 15-17, pH of the saliva from donors A-C were tested in sucrose challenged conditions as a function of zinc oxide/zinc citrate concentration. Buffering effects were clearly observed over the untreated control of donor B as shown in FIG. 16, but none of the zinc oxide/zinc citrate solutions in FIGS. 15-17 show a similar high level of buffering effect as the zinc oxide/zinc citrate/arginine solution.

Figure 18:
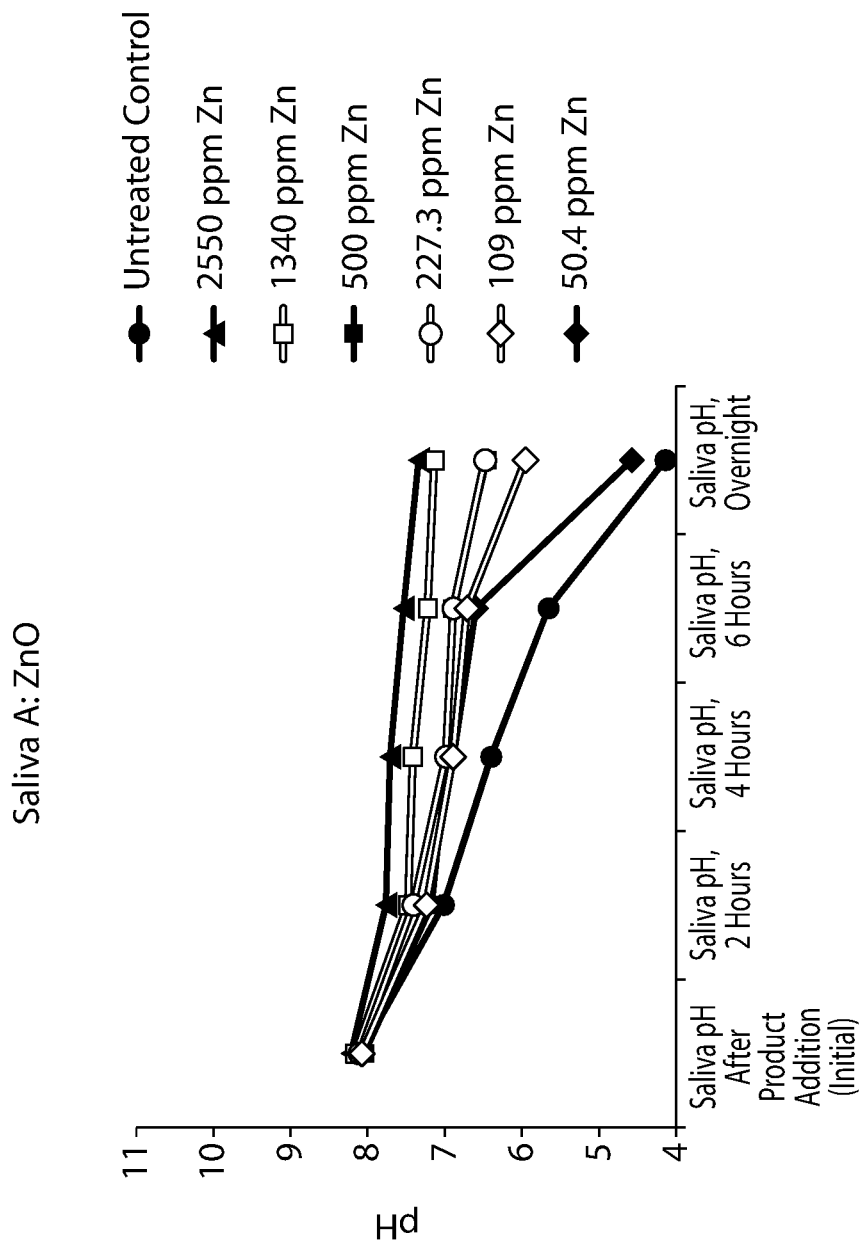
FIG. 18 illustrates the pH of whole saliva from a donor (Donor A) treated with zinc oxide solutions having various concentrations of zinc oxide after sucrose challenge as a function of time.
Figure 19:
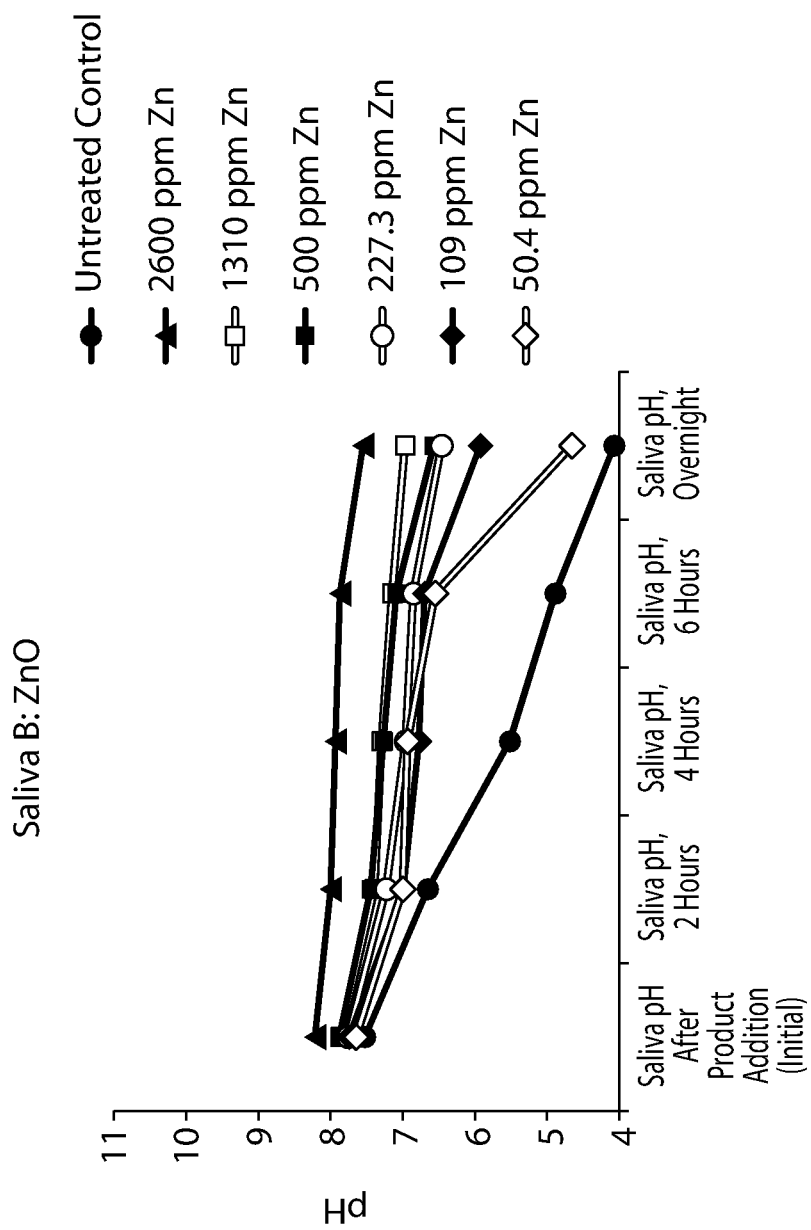
FIG. 19 illustrates the pH of whole saliva from a donor (Donor B) treated with zinc oxide solutions having various concentrations of zinc oxide after sucrose challenge as a function of time.
Figure 20:
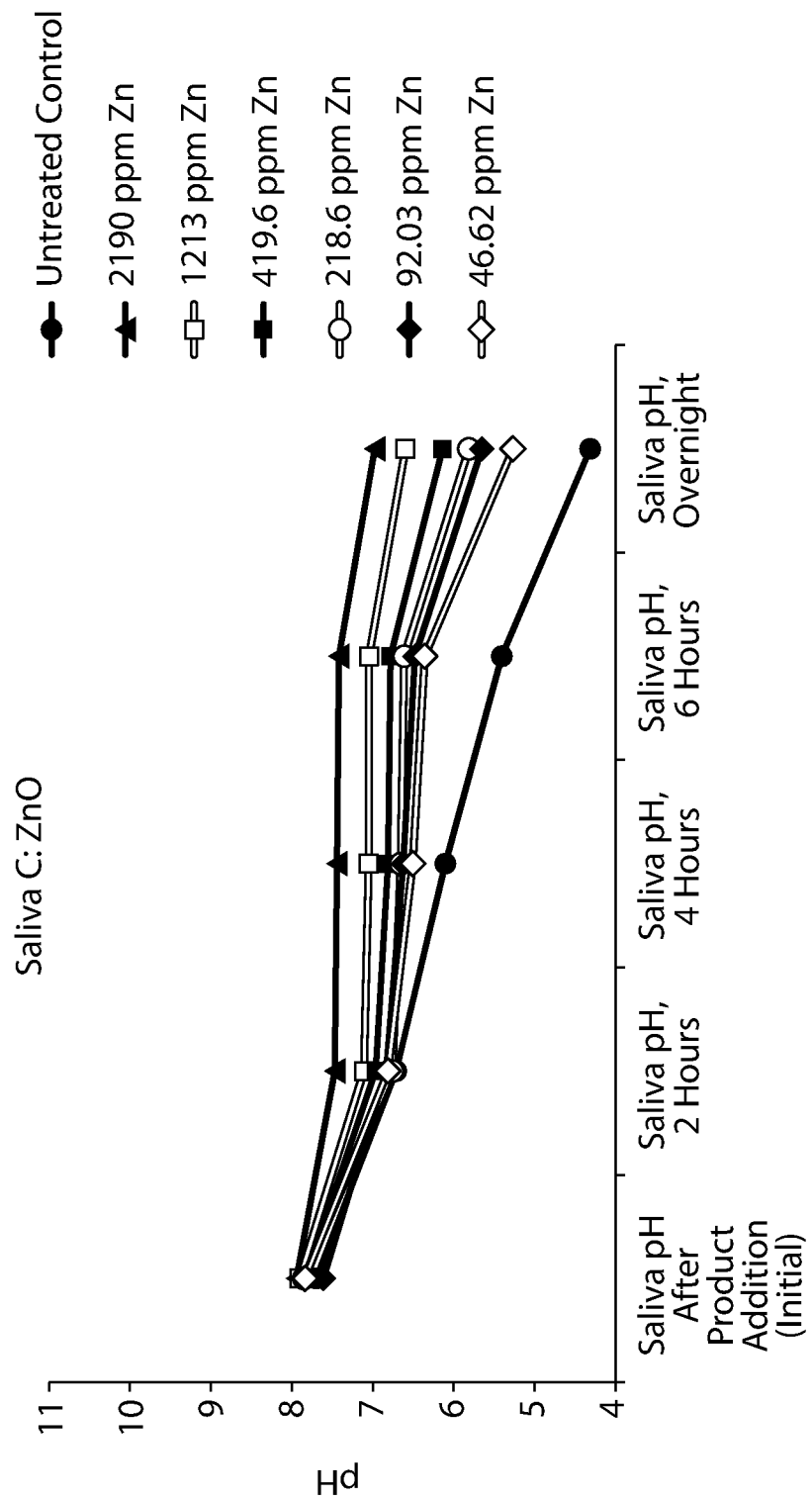
FIG. 20 illustrates the pH of whole saliva from a donor (Donor C) treated with zinc oxide solutions having various concentrations of zinc oxide after sucrose challenge as a function of time.

As shown in FIGS. 18-20, pH of the saliva from donors A-C were tested in sucrose challenged conditions as a function of zinc oxide concentration. Buffering effects were clearly observed over the untreated control of each of the donors, but none of the zinc oxide/zinc citrate solutions in FIGS. 18-20 show a similar high level of buffering effect as the zinc oxide/zinc citrate/arginine solution.

Figure 21:
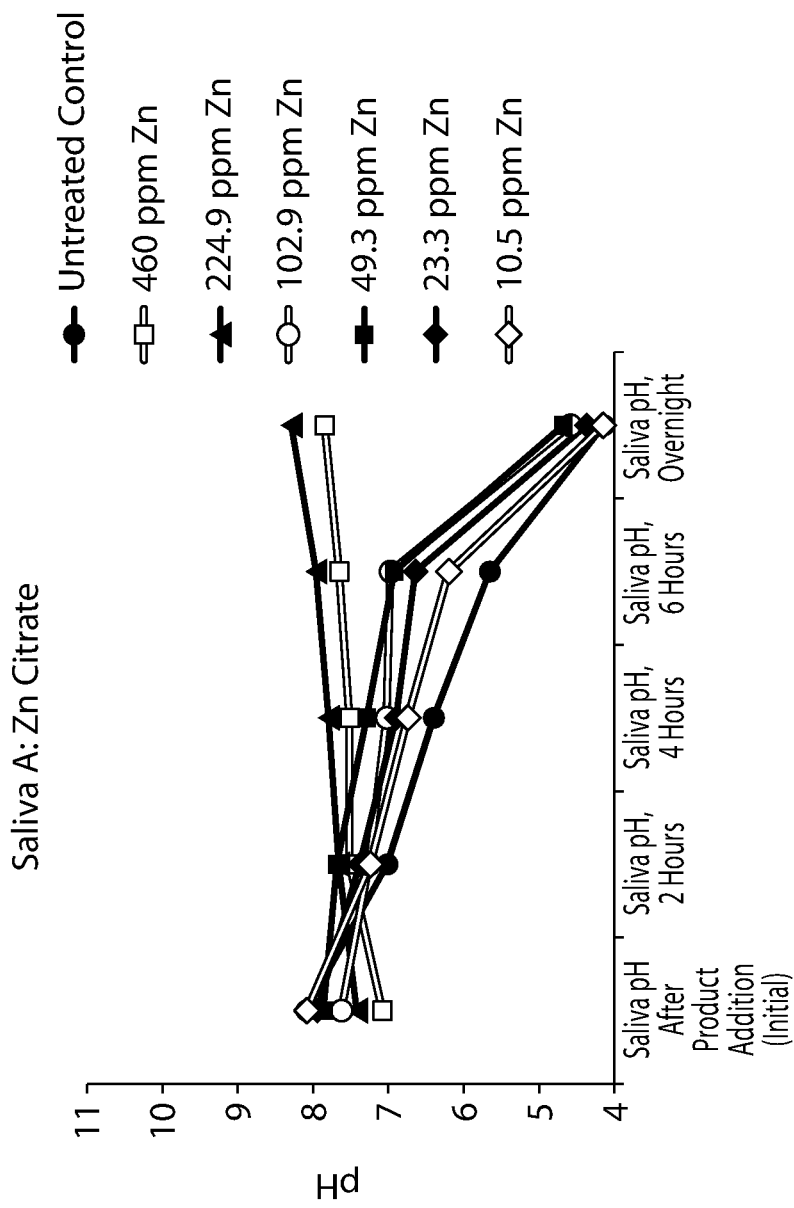
FIG. 21 illustrates the pH of whole saliva from a donor (Donor B) treated with zinc citrate solutions having various concentrations of zinc citrate after sucrose challenge as a function of time.
Figure 22:
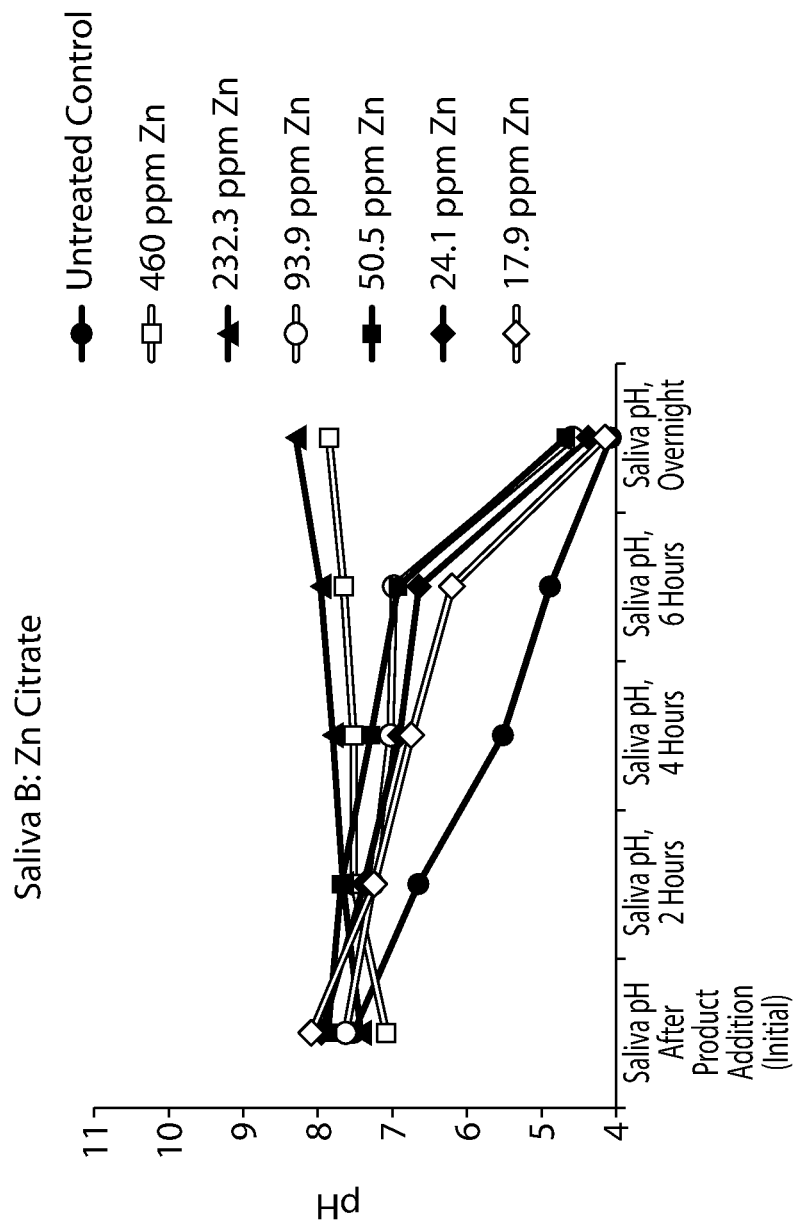
FIG. 22 illustrates the pH of whole saliva from a donor (Donor B) treated with zinc citrate solutions having various concentrations of zinc citrate after sucrose challenge as a function of time.
Figure 23:
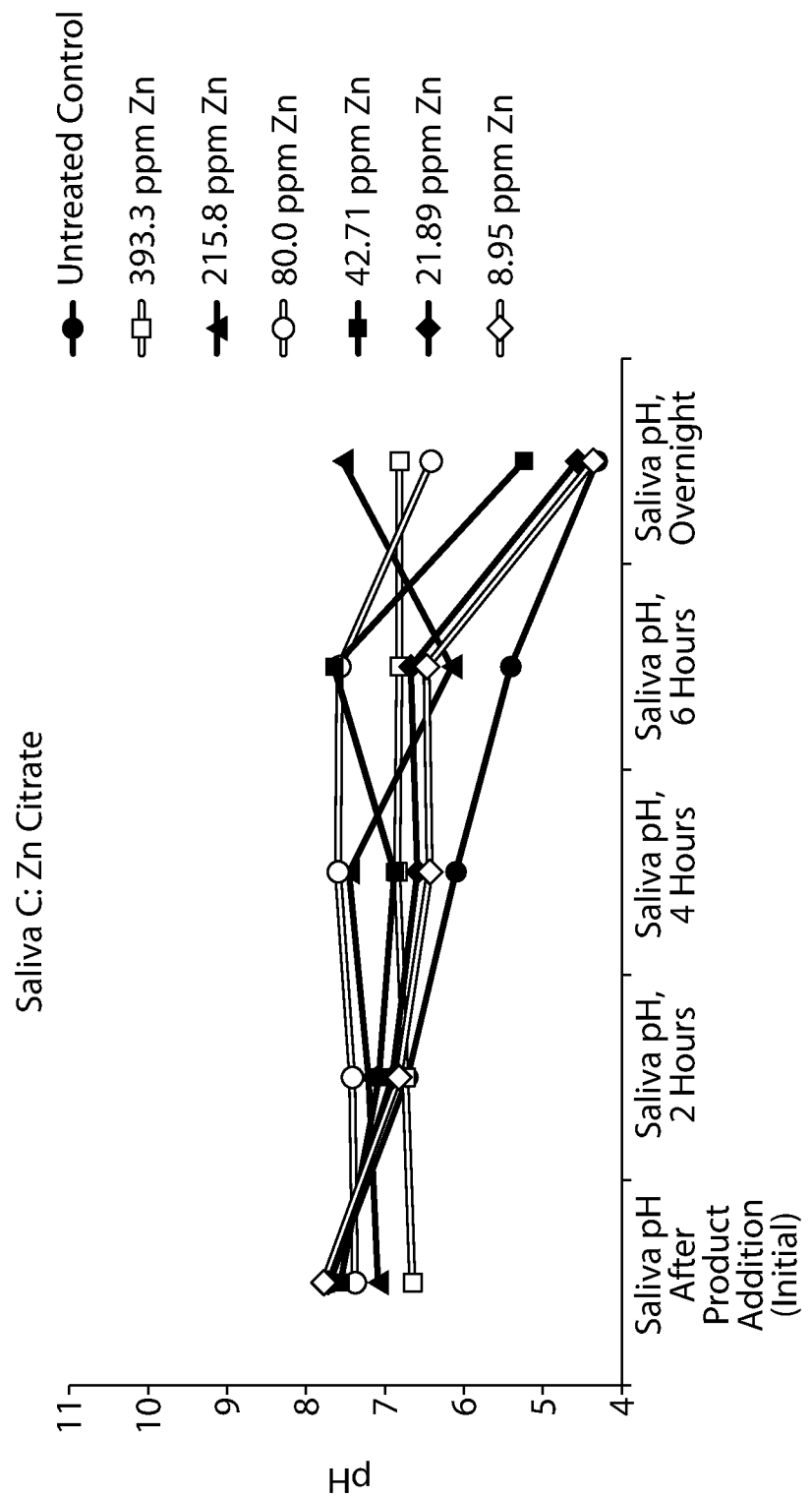
FIG. 23 illustrates the pH of whole saliva from a donor (Donor C) treated with zinc citrate solutions having various concentrations of zinc citrate after sucrose challenge as a function of time.

As shown in FIGS. 21-23, pH of the saliva from donors A-C were tested in sucrose challenged conditions as a function of zinc citrate concentration. Buffering effects were observed over the untreated control of each of the donors, but none of the zinc oxide/zinc citrate solutions in FIGS. 21-23 show a similar high level of buffering effect as the zinc oxide/zinc citrate/arginine solution.

Based on the above, it is apparent that zinc oxide/zinc citrate/arginine is has an effect on saliva buffering capacity. Without being bound by theory, the results indicate that zinc oxide/zinc citrate/arginine can prevent the activities or neutralize the products of acid-causing bacteria. Additionally, the effect on pH could attributed to the antibacterial effects of zinc oxide/zinc citrate/arginine.

Example 5—Representative Formulation

In one representative formulation, a dentifrice comprises the following:
 a. 1.0 wt. % zinc oxide
 b. 0.5 wt. % zinc citrate
 c. 1.5 wt. % L-arginine
 d. 0.32 wt. % sodium fluoride; and
 e. 35% wt. glycerin Example 6—Representative Dentifrice Formulation Representative Dentifrice Formulation:

| Ingredient | Formula 1 |
| --- | --- |
| DEMINERALIZED WATER | Q.S. |
| ABRASIVES | 10%-20% |
| 99.0%-101.0% GLYCERIN - USP, EP VEG | 35 |
| L-Arginine | 1.5 |
| AMPHOTERIC SURFACTANT | 1.0%-1.5% |
| NON-IONIC SURFACTANT | 0.25%-0.75% |
| POLYMERS | 0.75%-1.5% |
| ALKALI PHOSPHATE SALT | 0.25%-0.75% |
| ZINC CITRATE TRIHYDRATE | 0.5 |
| WHITENING AGENT | 0.25%-1.0% |
| FLAVORING AGENTS | 1.5%-1.9% |
| 85% SYRUPY PHOSPHORIC ACID - FOOD GRADE | 0-0.35 |
| SODIUM FLUORIDE - USP, EP | 0.32 |
| SILICA - THICKENER | 5%-7% |
| ANIONIC SURFACTANT | 1%-3% |
| ZINC OXIDE | 1 |
| PRESERVATIVE | 0.4 |
| Total Components | 100 |

While the present invention has been described with reference to embodiments, it will be understood by those skilled in the art that various modifications and variations may be made therein without departing from the scope of the present invention as defined by the appended claims.

The invention claimed is:
1. An oral care buffering composition comprising:
 a. a basic amino acid in free or salt form wherein the amino acid is arginine;
 b. zinc oxide and zinc citrate; and
 c. an orally acceptable carrier,
 wherein the oral care composition provides a buffering effect against acidic conditions in the oral cavity following acid challenge or sucrose challenge, wherein the buffering effect is greater than a corresponding buffering effect of compositions comprising arginine, zinc oxide or zinc citrate alone,
 wherein the composition is configured to be maintained at a pH over 7.0 when challenged in an acidic aqueous solution with 0.01M aqueous HCl in an amount of about 60% v/v based on the total volume of the solution.

2. The oral care composition of claim 1, wherein the composition maintains a pH over 5.0 when challenged in an acidic aqueous solution with a cola beverage in an amount of about 90% v/v based on the total volume of the solution.

3. The oral care composition of claim 1, wherein the composition maintains a pH over 3.9 when challenged in an acidic aqueous solution with a cola beverage in an amount of about 90% v/v based on the total volume of the solution.

4. The oral care composition of claim 1, wherein the composition maintains a pH over 3.0 when challenged in an acidic aqueous solution with a cola beverage in an amount of about 90% v/v based on the total volume of the solution.

5. The oral care composition of claim 1, wherein the composition maintains a pH over 5.5 when challenged in an acidic aqueous solution with a cola beverage in an amount of about 80% v/v based on the total volume of the solution.

6. The oral care composition of claim 1, wherein the composition maintains a pH over 4.0 when challenged in an acidic aqueous solution with orange juice in an amount of about 55% v/v based on the total volume of the solution.

7. The oral care composition of claim 1, wherein the composition maintains a pH over 6.0 when challenged in an acidic aqueous solution with orange juice in an amount of about 33% v/v based on the total volume of the solution.

8. The oral care composition of claim 1, wherein the composition maintains a pH over 5.0 when challenged in an acidic aqueous solution with orange juice in an amount of about 33% v/v based on the total volume of the solution.

9. The oral care composition of claim 1, wherein the composition maintains a pH over 8.0 when challenged in an acidic aqueous solution with 0.01M aqueous HCl in an amount of about 60% v/v based on the total volume of the solution.

10. The oral care composition of claim 1, wherein the composition maintains a pH over 7.0 6 hours after sucrose challenge.

11. The oral care composition of claim 1, wherein the composition maintains a pH over 8.0 6 hours after sucrose challenge.

12. The oral care composition of claim 1, wherein the composition maintains a pH over 9.0 6 hours after sucrose challenge.

13. The oral care composition of claim 1, wherein the composition maintains a pH over 7.0 24 hours after sucrose challenge.

14. The oral care composition of claim 1, wherein the composition maintains a pH over 8.0 24 hours after sucrose challenge.

15. The oral care composition of claim 1, wherein the composition maintains a pH over 9.0 24 hours after sucrose challenge.

16. The oral care composition of claim 1, wherein the arginine has the L-configuration.

17. The oral care composition of claim 1 wherein the amino acid is arginine from about 1.5 wt. %.

18. The oral care composition of claim 1, wherein the zinc citrate is in an amount of about 0.5 wt % and zinc oxide is present in an amount of about 1.0% based on the weight of the oral care composition.

* * * * *